(12) United States Patent
Nguyen et al.

(10) Patent No.: US 6,945,980 B2
(45) Date of Patent: Sep. 20, 2005

(54) MULTIPLE LOOP TISSUE CONNECTOR APPARATUS AND METHODS

(75) Inventors: John D. Nguyen, San Jose, CA (US); Liem Ho, Mountain View, CA (US); Cong Thach, San Jose, CA (US); Laurent Schaller, Los Altos, CA (US); Nga Doan, San Jose, CA (US)

(73) Assignee: Medtronic, Inc., Minneapolis, MN (US)

( * ) Notice: Subject to any disclaimer, the term of this patent is extended or adjusted under 35 U.S.C. 154(b) by 329 days.

(21) Appl. No.: 09/828,335

(22) Filed: Apr. 5, 2001

(65) Prior Publication Data

US 2001/0018593 A1 Aug. 30, 2001

Related U.S. Application Data

(63) Continuation-in-part of application No. 09/260,623, filed on Mar. 1, 1999, now Pat. No. 6,613,059, and a continuation-in-part of application No. 09/090,305, filed on Jun. 3, 1998, now Pat. No. 6,641,593.

(51) Int. Cl.$^7$ ............................................. A61B 17/08
(52) U.S. Cl. ....................................... 606/151; 606/153
(58) Field of Search ................................ 606/153, 179, 606/184, 157–159, 139, 141, 142, 151–152, 213, 222–224, 232, 191, 198, 200, 144, 228

(56) References Cited

U.S. PATENT DOCUMENTS

| | | |
|---|---|---|
| 43,098 A | 6/1864 | Cooper |
| 655,190 A | 8/1900 | Bramson |
| 1,583,271 A | 5/1926 | Biro |
| 1,625,602 A | 4/1927 | Gould et al. |
| 2,240,330 A | 4/1941 | Flagg et al. |
| 2,256,382 A | 9/1941 | Dole |
| 2,264,679 A | 12/1941 | Ravel |
| 2,516,710 A | 7/1950 | Mascolo |
| 2,715,486 A | 8/1955 | Marcoff-Moghadam et al. |
| 2,890,519 A | 6/1959 | Storz, Jr. |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |

(Continued)

FOREIGN PATENT DOCUMENTS

| | | |
|---|---|---|
| DE | 21 99 99 | 3/1910 |
| DE | 27 03 529 | 1/1977 |
| DE | 32 03 410 A1 | 5/1981 |

(Continued)

OTHER PUBLICATIONS

International Search Report PCT/US02/10865.
Internatioanl Preliminary Examination Report PCT/US02/10865.
Emery et al. "Suture Techniques for MIDCAB Surgery" Chapt. 12, pp. 87–91.

(Continued)

*Primary Examiner*—(Jackie) Tan-Uyen T. Ho
(74) *Attorney, Agent, or Firm*—Tom Berry; Jeffrey J. Hohenshell

(57) ABSTRACT

A tissue connector assembly comprising a multiple loop fastener movable between an open configuration and a closed configuration and a restraining device attached to the fastener for restraining the fastener in its open configuration provides for a self-closing, multiple suture fastener. A needle may be releasably attached to the fastener. A method for connecting tissues is also disclosed. The method includes inserting a fastener through tissue with the fastener being biased in an open position by a restraining device secured to the fastener, threading the fastener through more than one stitch, and removing the restraining device from the fastener.

14 Claims, 24 Drawing Sheets

U.S. PATENT DOCUMENTS

| | | |
|---|---|---|
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,875,648 A | 4/1975 | Bone |
| 3,910,281 A | 10/1975 | Kletschka et al. |
| 3,958,576 A | 5/1976 | Komiya |
| 3,976,079 A | 8/1976 | Samuels et al. |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,549,545 A | 10/1985 | Levy |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,719,924 A | 1/1988 | Crittenden et al. |
| 4,730,615 A | 3/1988 | Sutherland et al. |
| 4,809,695 A | 3/1989 | Gwathmey et al. |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,983,176 A | 1/1991 | Cushman et al. |
| 4,990,152 A | 2/1991 | Yoon |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,074,874 A | 12/1991 | Yoon, Inbae et al. |
| 5,100,418 A | 3/1992 | Yoon et al. |
| 5,123,913 A | 6/1992 | Wilk et al. |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,236,440 A | 8/1993 | Hlavacek |
| 5,242,456 A | 9/1993 | Nash et al. |
| 5,242,457 A | 9/1993 | Akopov et al. |
| 5,246,443 A | 9/1993 | Mai |
| 5,258,011 A | 11/1993 | Drews |
| 5,269,783 A | 12/1993 | Sander |
| 5,290,289 A | 3/1994 | Sanders et al. |
| 5,304,204 A | 4/1994 | Bregen |
| 5,312,436 A | 5/1994 | Coffey et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,383,904 A | 1/1995 | Totakura et al. |
| 5,403,346 A | 4/1995 | Loeser |
| 5,437,680 A | 8/1995 | Yoon |
| 5,437,685 A | 8/1995 | Blasnik |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,454,834 A | * 10/1995 | Boebel et al. ............... 606/228 |
| 5,456,246 A | 10/1995 | Schmieding et al. |
| 5,462,561 A | 10/1995 | Voda |
| 5,474,557 A | 12/1995 | Mai |
| 5,480,405 A | 1/1996 | Yoon |
| 5,486,197 A | 1/1996 | Le et al. |
| 5,499,990 A | 3/1996 | Schulken et al. |
| 5,500,000 A | 3/1996 | Feagin et al. |
| 5,527,342 A | 6/1996 | Pietrzak et al. |
| 5,549,619 A | 8/1996 | Peters et al. |
| 5,569,274 A | 10/1996 | Rapacki et al. |
| 5,569,301 A | 10/1996 | Granger et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Bennett et al. |
| 5,632,752 A | 5/1997 | Buelna |
| 5,632,753 A | 5/1997 | Loeser |
| 5,643,295 A | 7/1997 | Yoon |
| 5,645,568 A | 7/1997 | Chervitz et al. |
| 5,665,109 A | 9/1997 | Yoon |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,728,135 A | 3/1998 | Bregen et al. |
| 5,735,290 A | 4/1998 | Sterman et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,849,019 A | 12/1998 | Yoon |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,394 A | 4/1999 | Kienzle et al. |
| 5,941,434 A | 8/1999 | Green |
| 5,941,888 A | 8/1999 | Wallace et al. |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischmann et al. |

| | | | | | |
|---|---|---|---|---|---|
| 5,989,242 A | 11/1999 | Saadat et al. | EP | 0 641 546 A1 | 3/1995 |
| 5,989,268 A | 11/1999 | Pugsley, Jr. et al. | EP | 0 711 532 A1 | 5/1996 |
| 5,997,556 A | 12/1999 | Tanner | EP | 0 734 697 A2 | 10/1996 |
| 6,001,110 A | 12/1999 | Adams | EP | 0 778 005 A1 | 6/1997 |
| 6,013,084 A | 1/2000 | Ken et al. | EP | 0 815 795 A1 | 1/1998 |
| 6,074,401 A | 6/2000 | Gardiner et al. | GB | 2 223 410 A | 4/1990 |
| 6,132,438 A | 10/2000 | Fleischman et al. | JP | 10337291 | 12/1998 |
| 6,139,540 A | 10/2000 | Rost et al. | RU | 2110222 C1 | 5/1998 |
| 6,143,004 A | 11/2000 | Davis et al. | SU | 1186199 A | 10/1985 |
| 6,149,658 A | 11/2000 | Gardiner et al. | SU | 1456109 A1 | 2/1989 |
| 6,176,413 B1 | 1/2001 | Heck et al. | SU | 1560133 A1 | 4/1990 |
| 6,190,373 B1 | 2/2001 | Palermo et al. | WO | WO 90/06725 A1 | 6/1990 |
| 6,193,733 B1 | 2/2001 | Adams | WO | WO 90/09149 A1 | 8/1990 |
| 6,193,734 B1 | 2/2001 | Bolduc et al. | WO | WO 90/14795 A1 | 12/1990 |
| 6,254,615 B1 | 7/2001 | Bolduc et al. | WO | WO 91/07916 A1 | 6/1991 |
| 6,296,656 B1 | 10/2001 | Bolduc et al. | WO | WO 91/17712 A1 | 11/1991 |
| 6,346,112 B2 | 2/2002 | Adams | WO | WO 92/05828 A1 | 4/1992 |
| 6,514,265 B2 | 2/2003 | Ho et al. | WO | WO 94/15535 A1 | 7/1994 |
| 6,551,332 B1 | 4/2003 | Nguyen et al. | WO | WO 94/15537 A1 | 7/1994 |
| 6,607,541 B1 | 8/2003 | Gardiner et al. | WO | WO 96/00035 A1 | 1/1996 |
| 6,613,059 B2 | 9/2003 | Schaller et al. | WO | WO 96/06565 A1 | 3/1996 |
| 6,641,593 B1 | 11/2003 | Schaller et al. | WO | WO 96/38090 A1 | 12/1996 |
| 6,695,859 B1 | 2/2004 | Golden et al. | WO | WO 97/28744 A1 | 8/1997 |
| 2001/0018592 A1 | 8/2001 | Schaller et al. | WO | WO 97/32526 A1 | 9/1997 |
| 2003/0074012 A1 | 4/2003 | Nguyen et al. | WO | WO 97/42881 A1 | 11/1997 |
| 2004/0111099 A1 | 6/2004 | Nguyen et al. | WO | WO 98/30153 A1 | 7/1998 |
| | | | WO | WO 98/42262 A1 | 10/1998 |
| | FOREIGN PATENT DOCUMENTS | | WO | WO 02/13702 A1 | 2/2002 |
| DE | 32 27 984 A1 | 2/1984 | | | |
| DE | 41 33 800 C1 | 10/1991 | | | |
| DE | 44 02 058 C1 | 4/1995 | | | |
| DE | 195 47 617 C1 | 9/1997 | | | |
| EP | 0 140 557 A2 | 5/1985 | | | |
| EP | 0 121 362 B1 | 9/1987 | | | |
| EP | 0 432 692 A1 | 6/1991 | | | |
| EP | 0 478 949 B1 | 8/1991 | | | |
| EP | 0 494 636 A1 | 7/1992 | | | |
| EP | 0 537 955 B1 | 4/1993 | | | |
| EP | 0 559 429 A1 | 9/1993 | | | |
| EP | 0 326 426 B1 | 12/1994 | | | |
| EP | 0 419 597 B1 | 12/1994 | | | |

OTHER PUBLICATIONS

VCS Clip Applier System, published in 1995 by Auto Suture Company, a Division of U.S. Surgical Corporation (8 page).
Wylie et al., Edwin J., Manual of Vascular Surgery, (Springer–Verlag New York), (1980) Table of contents only.
International Search Report PCT/US99/12563.
Written Opinion PCT/US99/12563 dated Jun. 12, 2000.
International Search Report PCT/US99/12566.
Written Opinion PCT/US99/12566 dated Jul. 28, 2000.

* cited by examiner

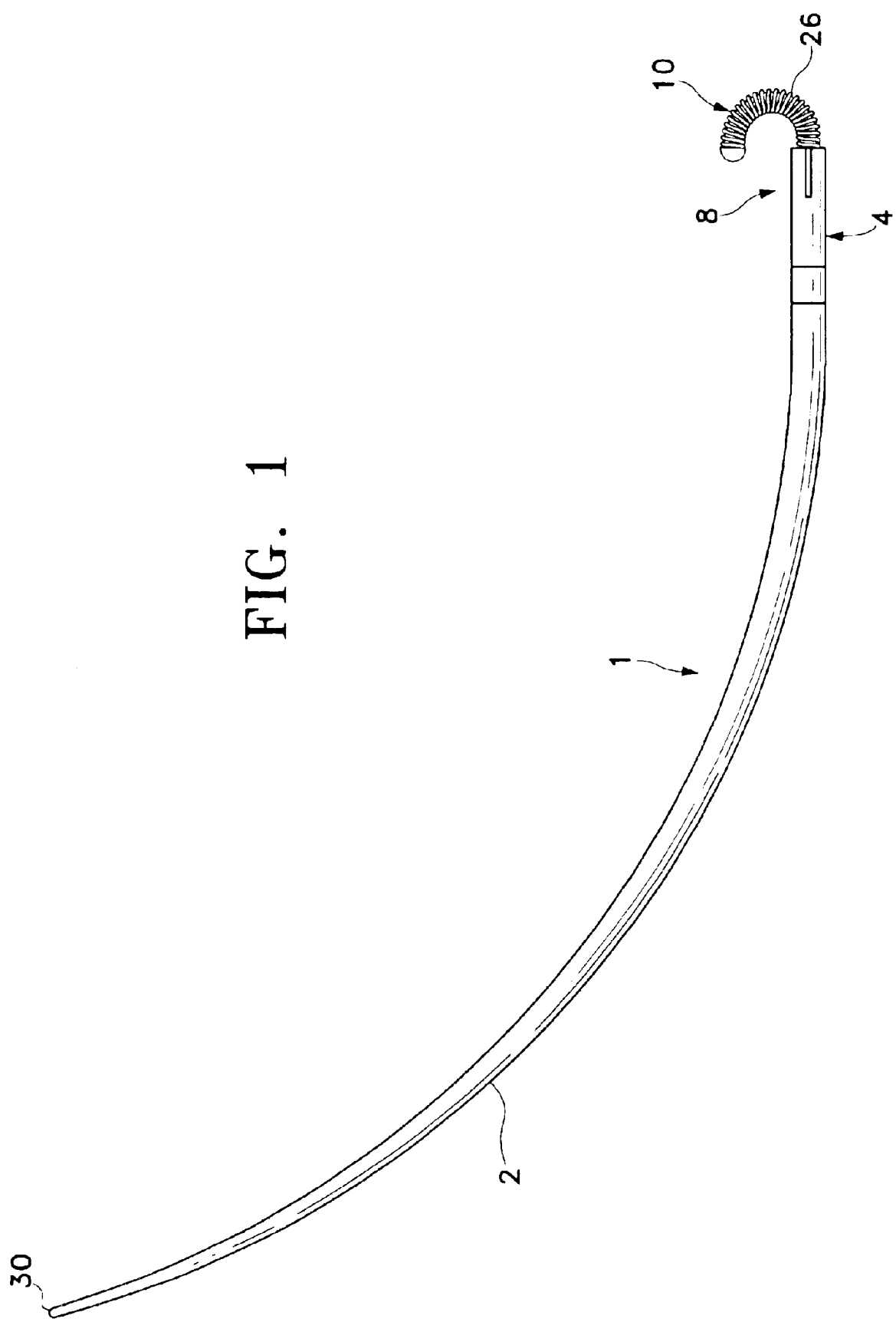

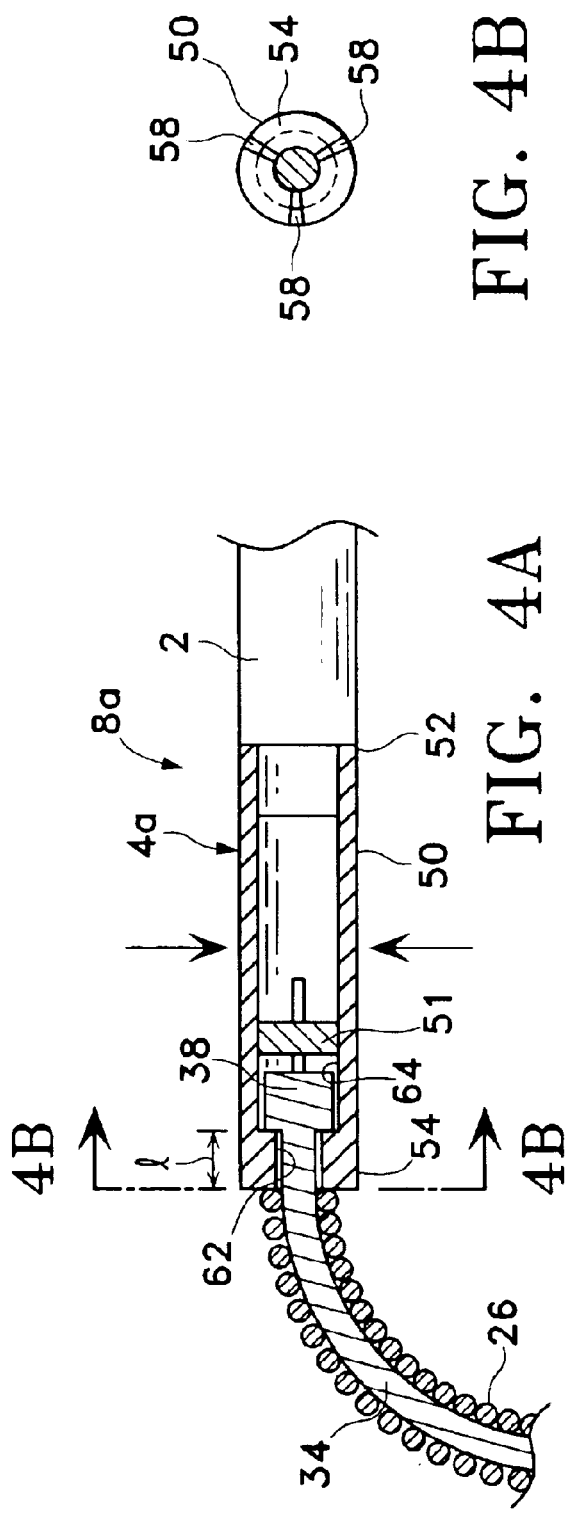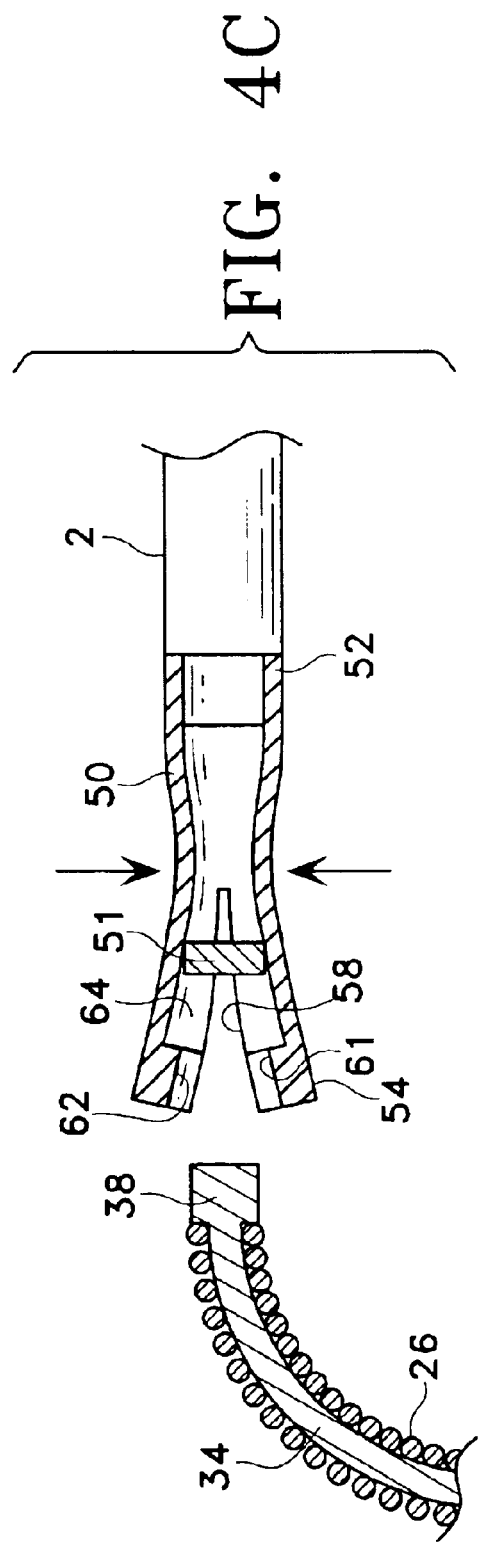

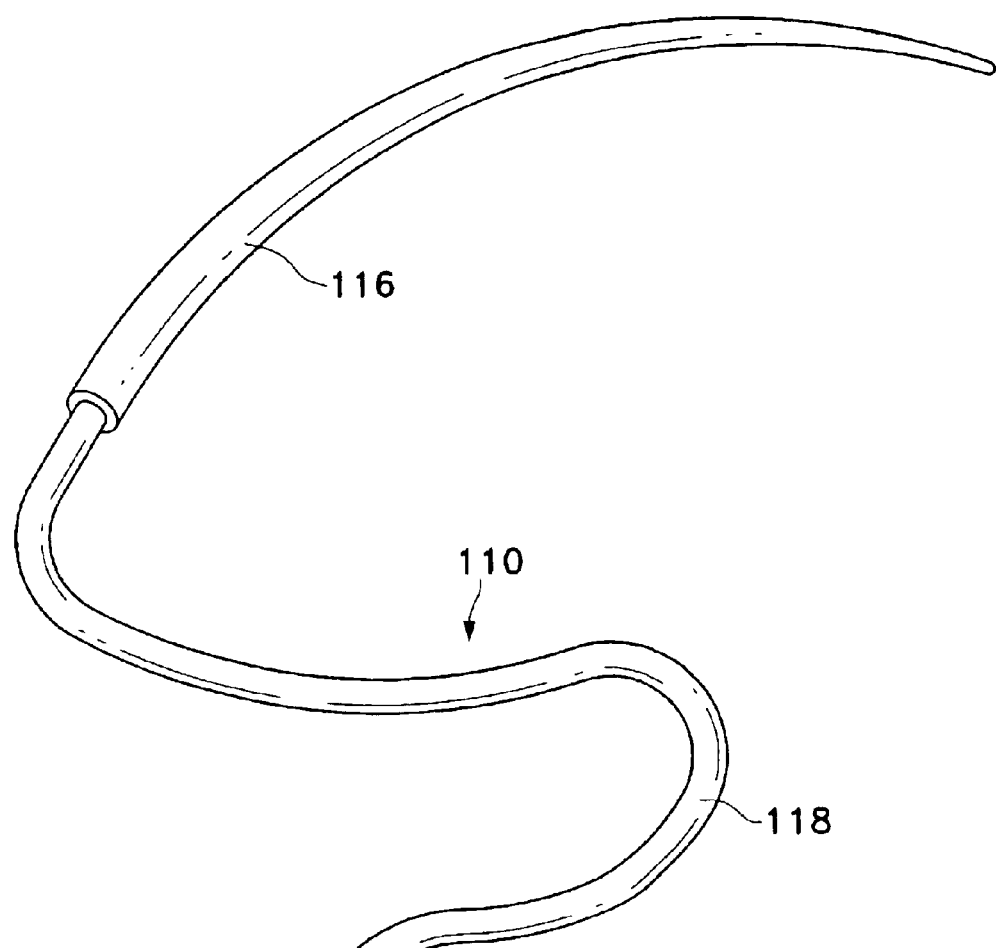
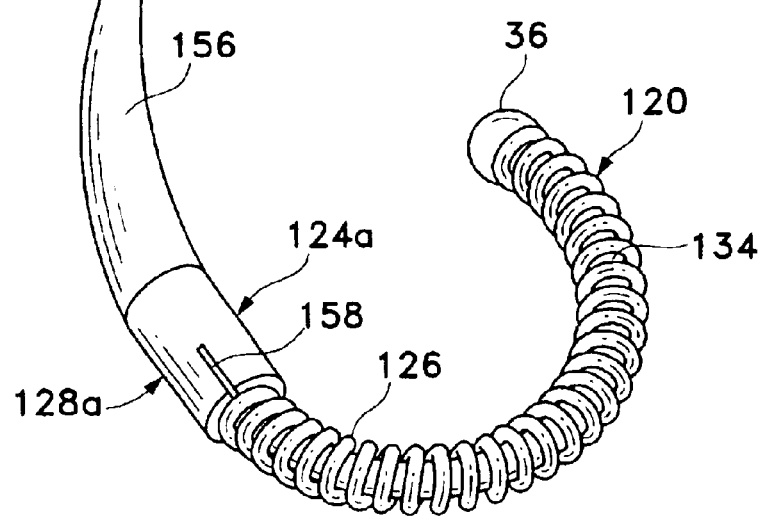
FIG. 6

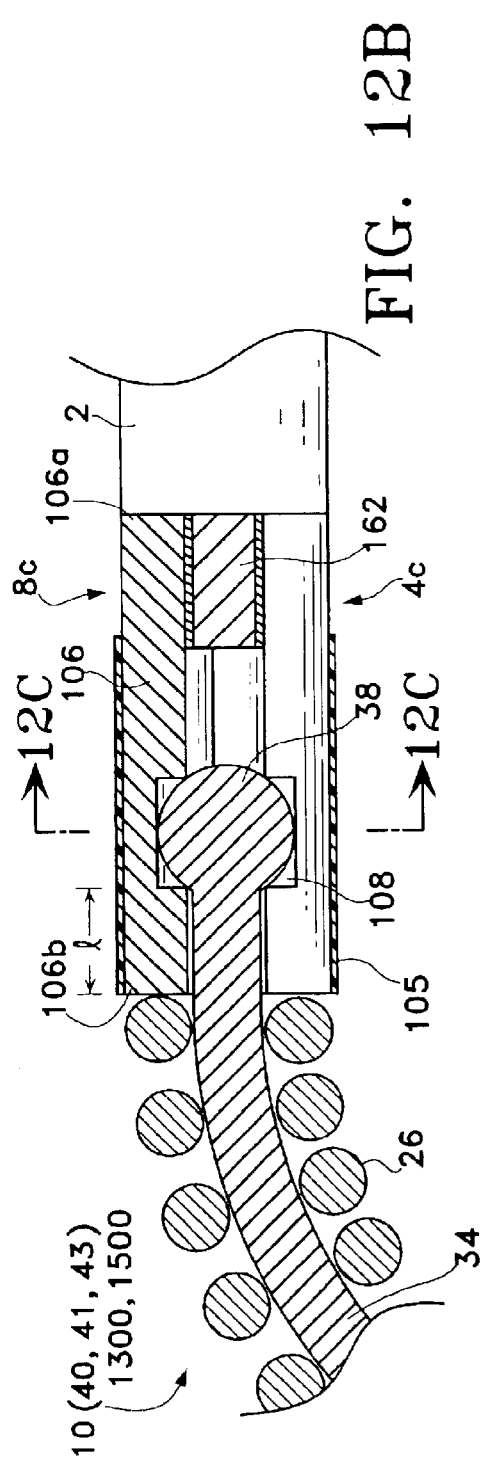
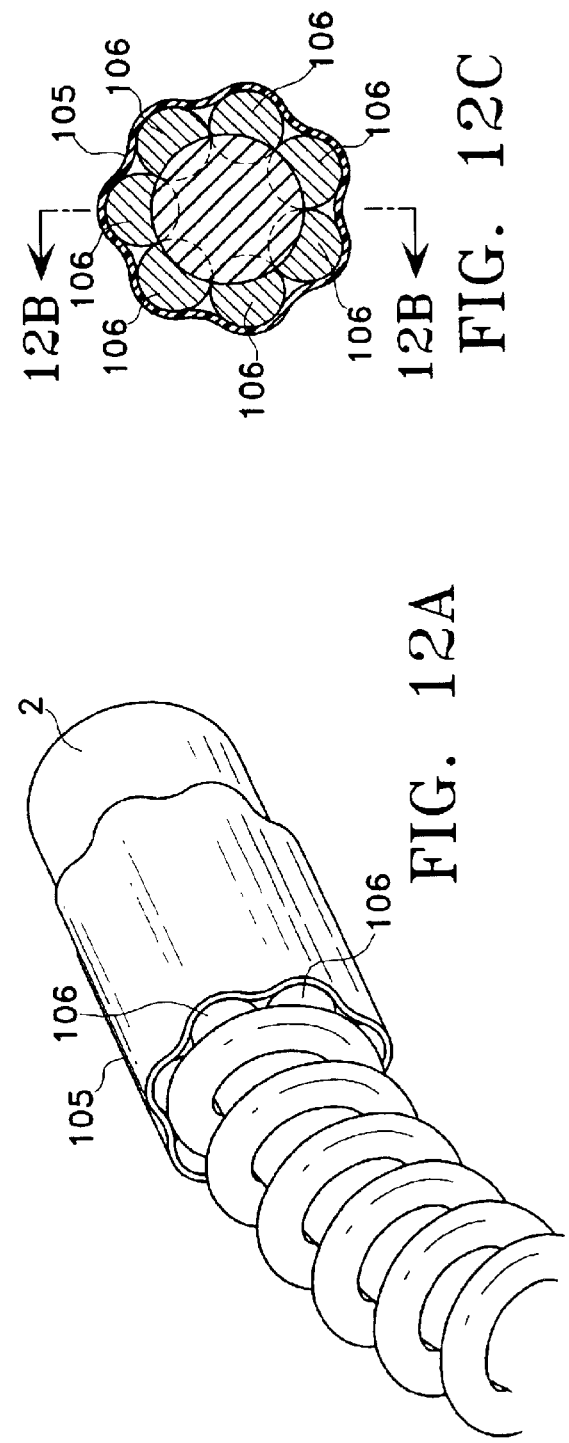
FIG. 12A
FIG. 12B
FIG. 12C

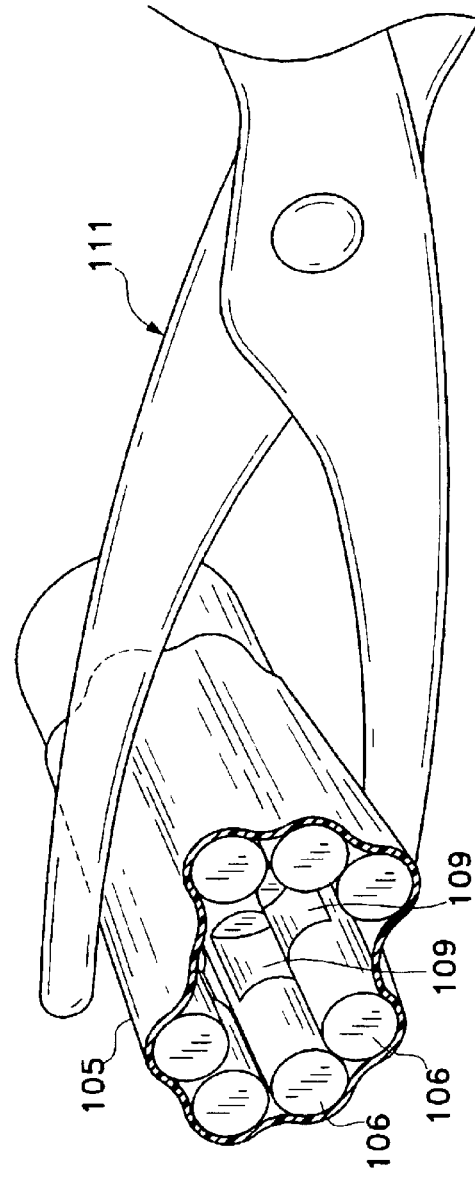
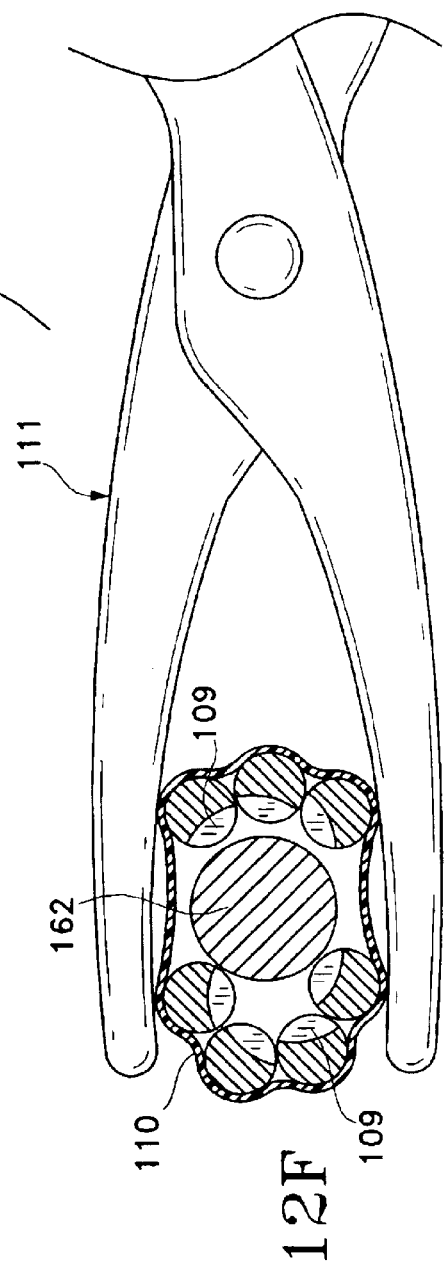

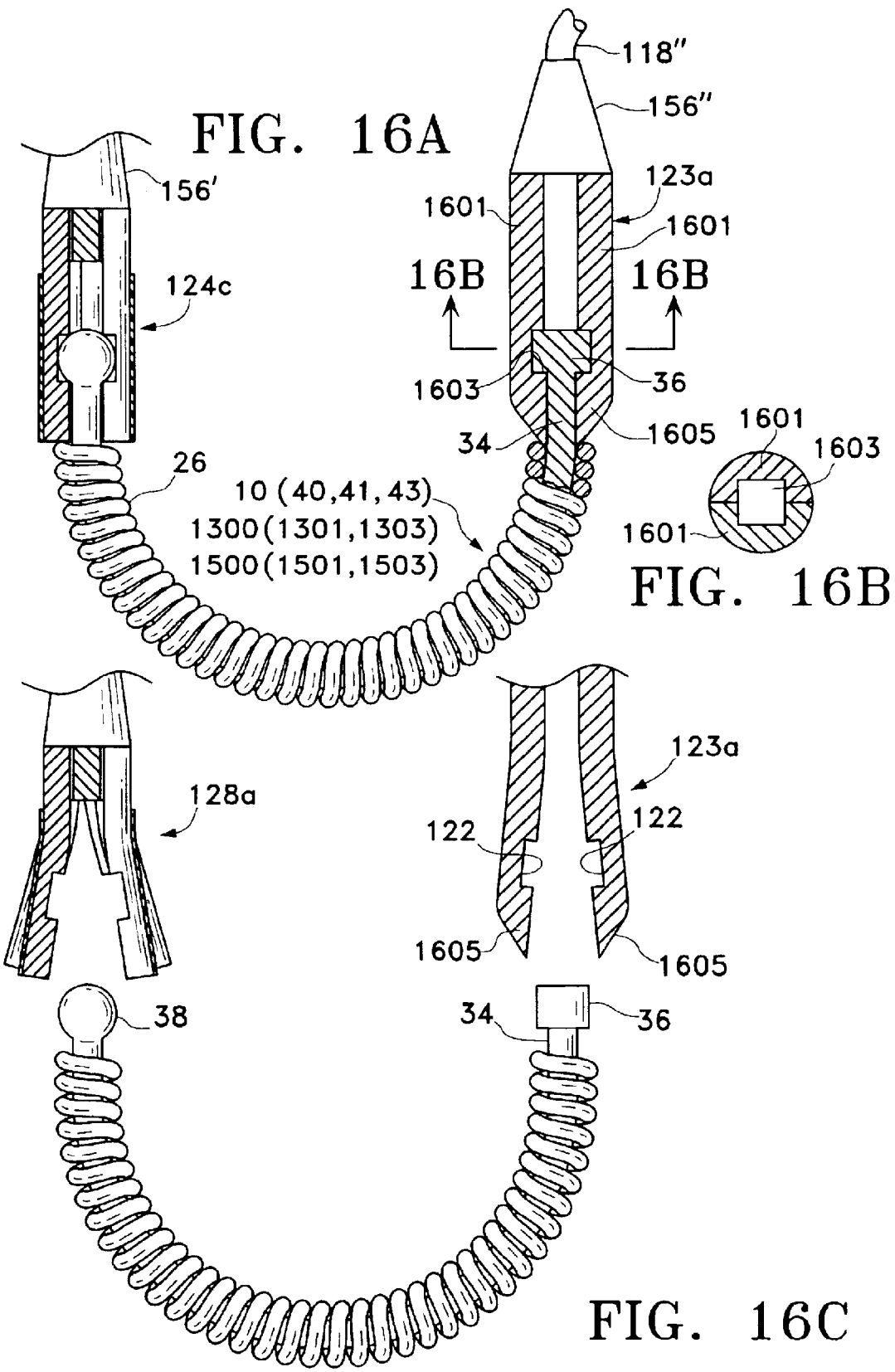

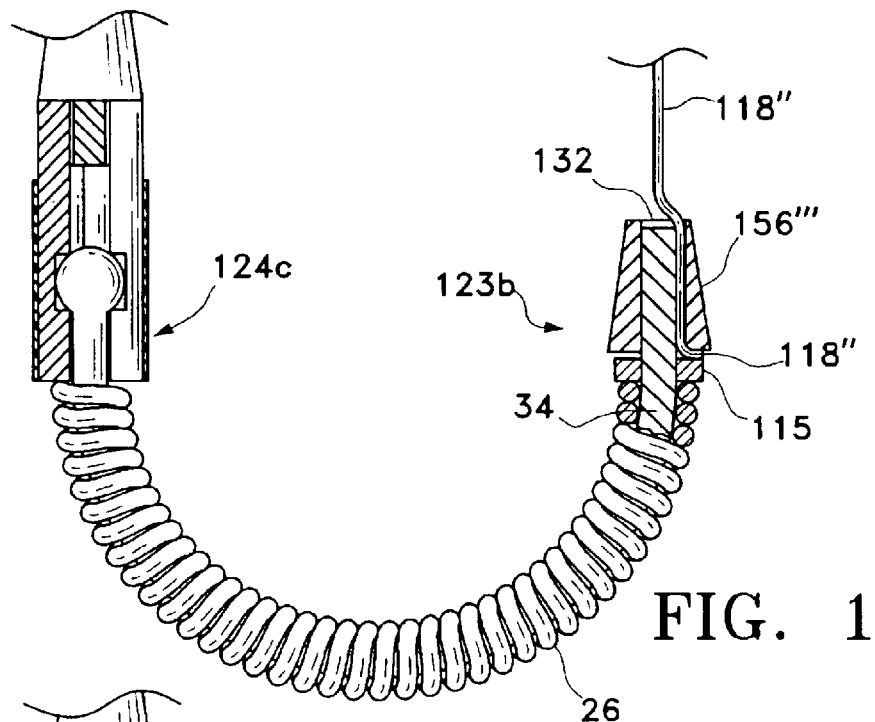
FIG. 16D
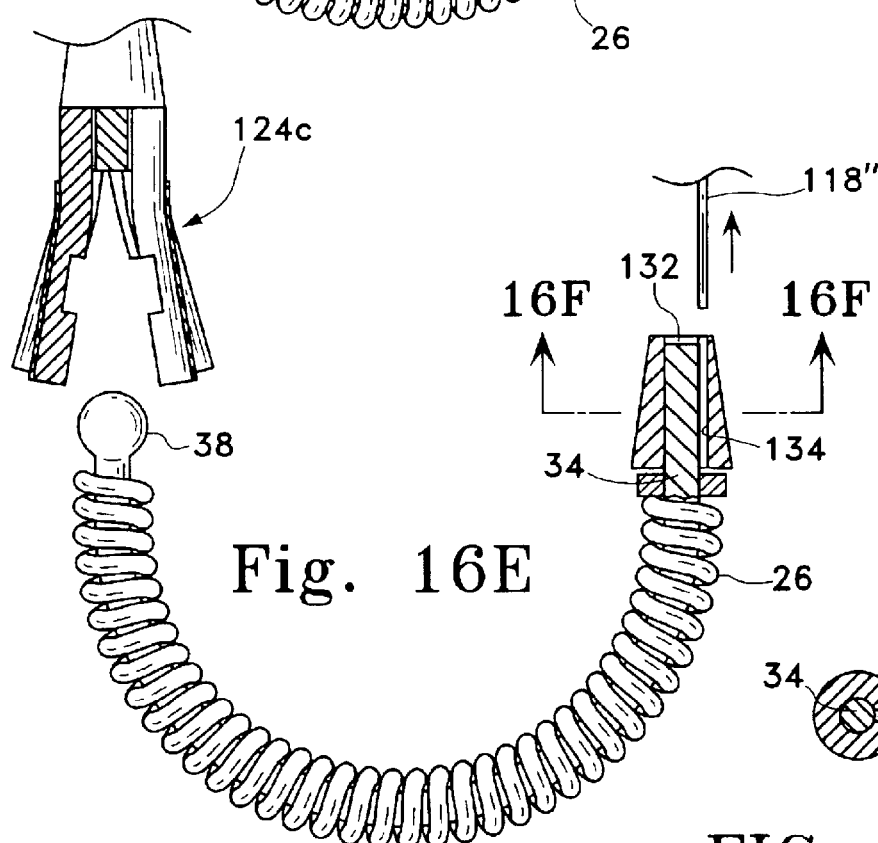
Fig. 16E
FIG. 16F

MULTIPLE LOOP TISSUE CONNECTOR APPARATUS AND METHODS

CROSS-REFERENCE TO RELATED DOCUMENTS

The present application is a continuation-in-part of patent applications Ser. No. 09/090,305, filed Jun. 3, 1998, now U.S. Pat. No. 6,641,593 and Ser. No. 09/260,623, filed Mar. 1, 1999, now U.S. Pat. No. 6,613,059.

FIELD OF THE INVENTION

The present invention relates to instruments and methods for connecting body tissues, or body tissue to prostheses.

BACKGROUND OF THE INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar, which is a pointed, piercing device, is delivered into the body with a cannula. After the trocar pierces the abdominal or thoracic wall, it is removed and the cannula is left with one end in the body cavity, where the operation is to take place, and the other end opening to the outside. A cannula has a small inside diameter, typically 5–10 millimeters, and sometimes up to as much as 20 millimeters. A number of such cannulas are inserted for any given operation.

A viewing instrument, typically including a miniature video carmera, or optical telescope is inserted through one of these cannulas and a variety of surgical instruments and refractors are inserted through others. The image provided by the viewing device may be displayed on a video screen or television monitor, affording the surgeon enhanced visual control over the instrunents. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retropcritoneal space is particularly useful for operations on the aorta and spine or abdominal wall hernia.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from DACRON® (polyester fibers) or TEFLON® (fluorocarbon fibers)) or are prepared as autografts (from the patient's own tissues) or heterografts (from the tissues of animals) or a combination of tissues, semisynthetic tissues and or alloplastic materials. A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin S. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swaged on" to a long, trailing suture material. The needle must be precisely controlled and accurately placed through both graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for wide-spread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by applying an instrument about the tissue in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be properly positioned with respect to each other, for example by skewering the tissues with a needle as discussed above in common suturing techniques or with forceps to bring the tissues together. It is extremely difficult to perform such positioning techniques in minimally invasive procedures.

Therefore, there is currently a need for other tissue connector assemblies.

SUMMARY OF THE INVENTION

The present invention involves improvements to devices and methods for connecting tissues or tissue(s) and grafts, such as in a vascular anastomosis. The invention generally involves a surgical clip or fastener which is self-closing. Preferably, the surgical fastener comprises a shape memory material, most preferably nitinol.

According to one aspect of the invention, a tissue connector assembly is provided with a self-closing fastener movable between an open configuration and a closed configuration, and a restraining device attached to the fastener for restraining the fastener in its open configuration. The fastener may have a generally U-shaped configuration when in its open configuration. In one embodiment the restraining device can be uncoupled from the fastener, allowing the fastener to move from an open towards the closed configuration.

According to another aspect of the present invention, the fastener has one or more needles releasably attached to the fastener. In one embodiment the fastener is releasably coupled to one needle, and in a second embodiment the fastener is releasably coupled to two needles. In particular, each fastener end can have a separate release mechanism for releasing a needle.

According to yet another aspect of the present invention, the fastener is a wire that is held in an open configuration with a restraining device comprising a coil wrapped about the wire.

According to an aspect of the present invention, a fastener is provided for forming multiple stitches. In one embodiment, the fastener has an open and a closed configuration. The fastener in an open configuration can be threaded through multiple stitches through tissue. When the fastener is returned to a closed configuration, the fastener provides a closing force to the stitched tissue. In another embodiment the fastener has a restraining device and is attached to a needle. The needle is used to thread the open fastener through the stitches, while the release mechanisms separates the fastener from the needle and allows the fastener to assume a closed configuration having the shape of the stitches.

In another aspect of the invention, a locking device is provided for releasably locking the fastener in its open configuration. Upon release of the locking device a restraining force is removed from the fastener to allow the fastener to move to its unbiased, closed position. Advantageously, the locking device may also be arranged to removably connect a needle to the fastener. Upon release of the locking device, the needle is disconnected from the fastener. Both removal of the needle and release of the biasing force from the fastener may occur simultaneously.

In yet another aspect of the invention, the fastener includes a wire which, in one embodiment has a circular cross-section, and in another embodiment is a shape memory alloy.

A method of the present invention generally includes inserting a fastener through tissue with the fastener biased in an open position by a restraining device coupled to the fastener, and removing the restraining force on the fastener to allow the fastener to close. In one embodiment the fastener is maintained in an open configuration by a locking device and returns to a closed configuration upon release of the locking device.

Yet another aspect of the present invention provides a method of using a fastener to form multiple stitches. A self-closing fastener having a generally open configuration and a closed configuration in the form of a specified number and spacing of multiple stitches is provided. The fastener is stitched, through an attachment to a needle, through the specified stitches. The fastener is then actuated to allow the configuration to assume a closed configuration.

The above is a brief description of some deficiencies in the prior art and advantages of the present invention. Other features, advantages, and embodiments of the invention will be apparent to those skilled in the art from the following description, accompanying drawings, and claims.

BRIEF DESCRIPTION OF THE DRAWINGS

FIG. 1 is a front view of a tissue connector assembly of the present invention;

FIG. 3A shows the fastener in a closed position, FIG. 3B is a side view of the fastener of FIG. 3A, FIG. 3C is an enlarged view of the fastener in an open position, and FIG. 3D is an enlarged view of an alternate configuration of the fastener shown in a closed position;

FIG. 3E shows the fastener in a closed position, FIG. 3F is a side view of the fastener of FIG. 3E, and FIG. 3G is an enlarged view of an alternate configuration of the fastener shown in a closed position;

FIGS. 4A–4C is are cross-sectional views of a restraining device of the tissue connector assembly of FIG. 1, where FIG. 4A is a view of the assembly in a locked position, FIG. 4B is a cross-sectional view of the restraining device of FIG. 4A taken in the plane including line 4B—4B, and FIG. 4C is a cross-sectional view of the restraining device of FIG. 4A in an unlocked position;

FIG. 6 is a perspective of a second embodiment of a tissue connector assembly of the present invention;

FIGS. 12A–12F illustrates yet another restraining device, where FIG. 12A shows a perspective view of the restraining device coupled with a fastener of FIG. 1, FIG. 12B is a sectional view of the restraining device of FIG. 12A, FIG. 12C is a transverse cross-sectional view of the restraining device taken along line 12C—12C in FIG. 12B, FIG. 12D shows a perspective view of the restraining device coupled with a fastener of FIGS. 6 or 11, FIGS. 12E and 12F are perspective and end views of the restraining device, respectively, showing the device depressed for release of the fastener;

FIG. 14A shows the orientation of the tissues and the first piercing, FIG. 14B shows the threading of the fastener through the tissues, and FIG. 14C is a released fastener in the closed configuration of FIG. 13A;

FIGS. 16A–16C show a synchronized fastener release system, where FIGS. 16A and 16C are partial sectional views of the system in a coupled and decoupled state, respectfully, and FIG. 16B is a sectional view taken along lines 16B—16B in FIG. 16A;

FIGS. 16D–16F show another synchronized fastener release system where FIGS. 16D and 16E are partial sectional views of the system in a coupled and decoupled state, respectfully, and FIG. 16F is a transverse cross-sectional view taken along line 16F—16F in FIG. 16E;

FIG. 17A shows the orientation of the tissues and the piercings of the first needle, FIG. 17B shows the threading of the fastener through the tissues and the piercings of the second needle, FIG. 17C shows the fastener after threading through the tissue, and FIG. 17D is a released fastener in the closed configuration of FIG. 13A.

Corresponding reference characters indicate corresponding parts throughout the several views of the drawings.

DESCRIPTION OF THE INVENTION

Figure 2A:
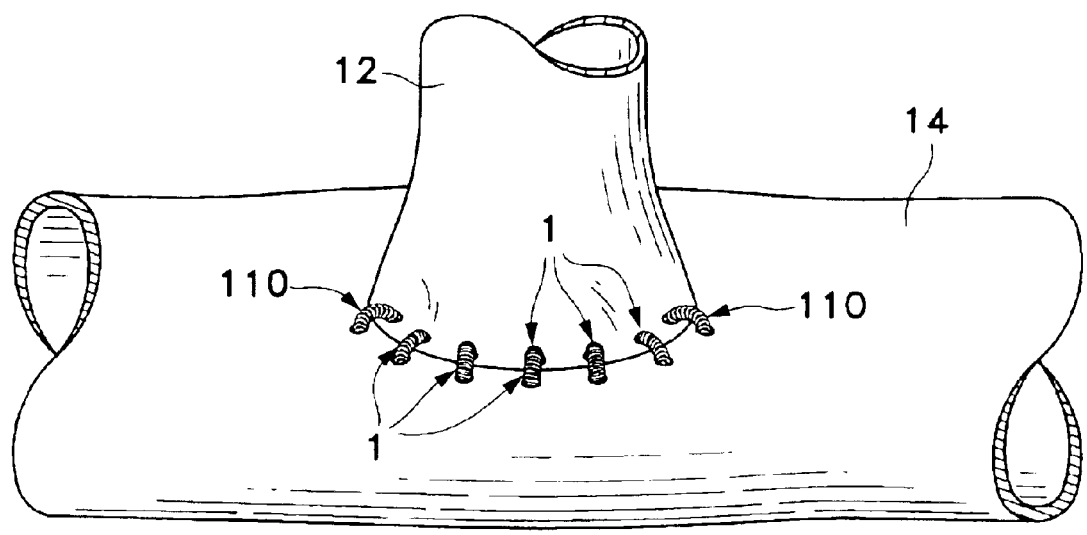
FIG. 2A shows a graft vessel connected to a target vessel with tissue connector assemblies of FIG. 1.

Referring now to the drawings, and first to FIG. 1, a tissue connector assembly constructed according to the principles of the present invention is shown and generally indicated with reference numeral 1. The tissue connector assembly 1 may be used to manipulate and align tissues, or tissue and graft with respect to each other and thereafter connect the tissues together (FIGS. 2A–2C, 7–10, 14 and 17). As used herein, the term graft includes any of the following: homografts, xenografts, allografts, alloplastic materials, and combinations of the foregoing. The tissue connector assembly 1 may be used in vascular surgery to replace or bypass a diseased, occluded, or injured artery by connecting a graft vessel 12 to a coronary artery 14 or vein in an anastomosis, for example. The tissue connector assembly 1 may be used in open surgical procedures or in minimally invasive or endoscopic procedures for attaching tissue located in the chest, abdominal cavity, or retroperitoneal space. These examples, however, are provided for illustration and are not meant to be limiting.

In the embodiment shown in FIG. 1, the tissue connector assembly 1 generally comprises a penetrating member 2, and fastener or surgical clip 10. A restraining device, generally indicated at 8 and comprising a spring (or coil) 26 and a locking device generally indicated at 4, is connected to the fastener 10 for holding the fastener in a deformed configuration as further described below. Activation of the restraining device 8 produces two effects: it allows fastener 10 to become unrestrained, allowing it to assume a differently, or undeformed, configuration, and acts as a release mechanism to separate fastener 10 from penetrating member 2.

The penetrating member or needle 2 has a sharp pointed tip 30 at its distal end for penetrating tissue. The needle 2 may be bent as shown in FIG. 1, for example. The distal end of the needle 2 is preferably rigid to facilitate penetration of tissue. The remaining length of the needle 2 may be rigid or flexible to facilitate movement of the needle through the tissue as further described below. The tip 30 of the needle 2 may be conical, tapered, or grounded to attain a three or four facet tip, for example. The needle 2 may be made from stainless steel or any other suitable material, such as a polymeric material. It is to be understood that the needle 2 may have a shape or radius of curvature other than the one shown, without departing from the scope of the invention. The needle 2 may be integrally formed with the locking device 4 or may be swaged, welded, threadably attached, or attached by any other suitable means to the locking device.

Figure 2B:
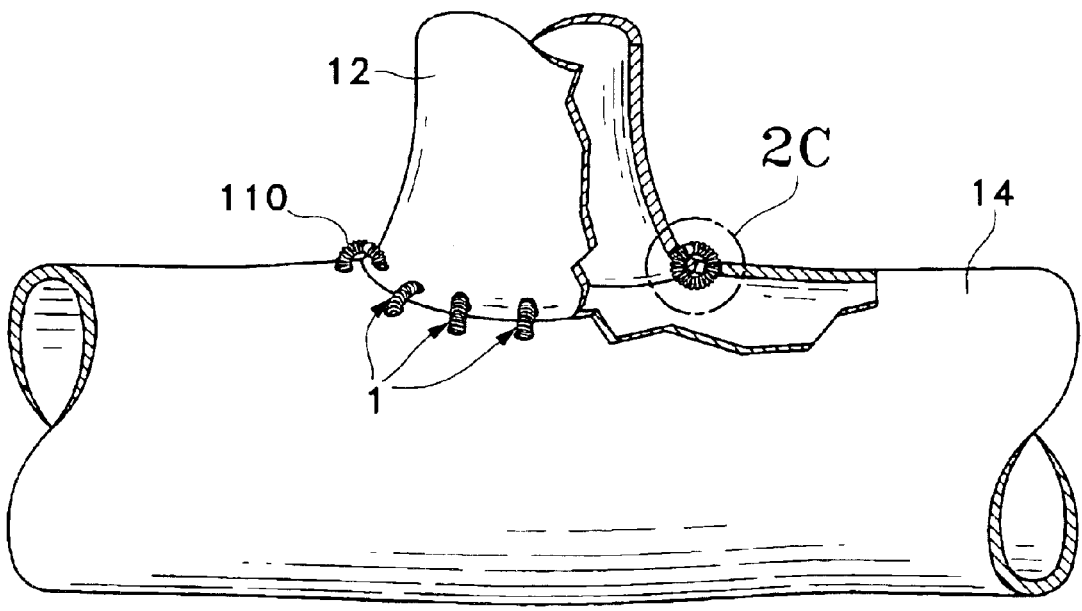
FIG. 2B is a front view of the connected graft and target vessels of FIG. 2A, with portions broken away to show detail.
Figure 2C:
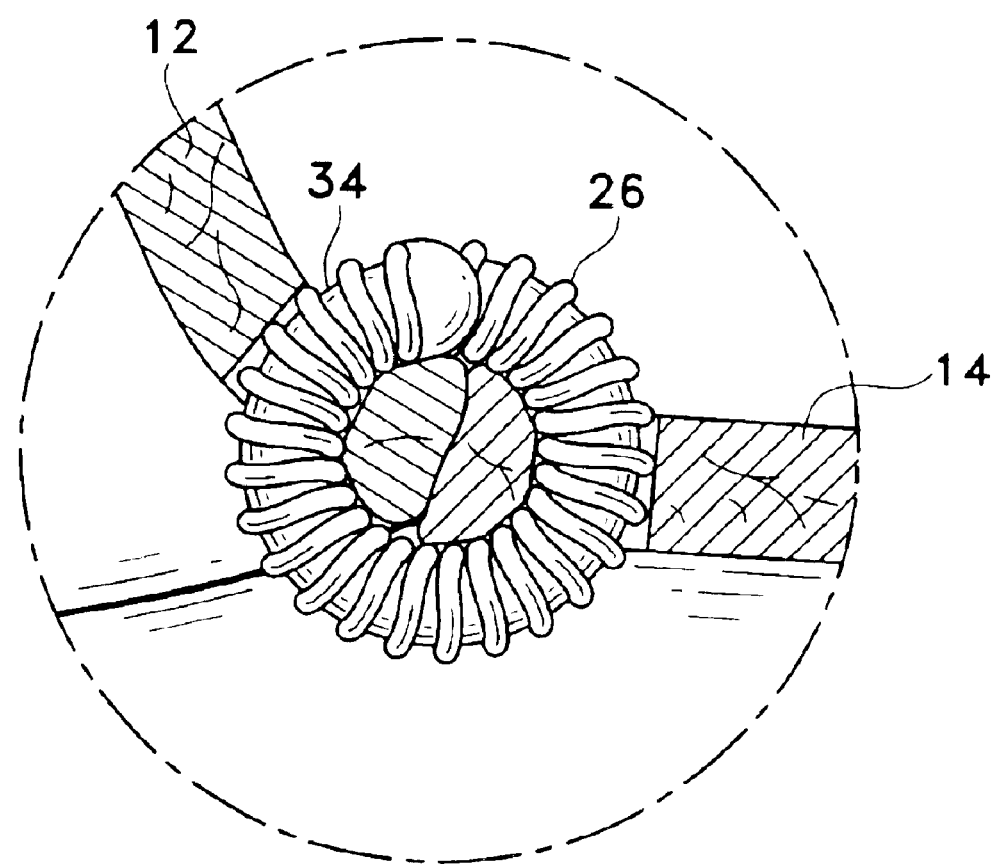
FIG. 2C is an enlarged view of the tissue connection shown in FIG. 2B.
Figure 3A:
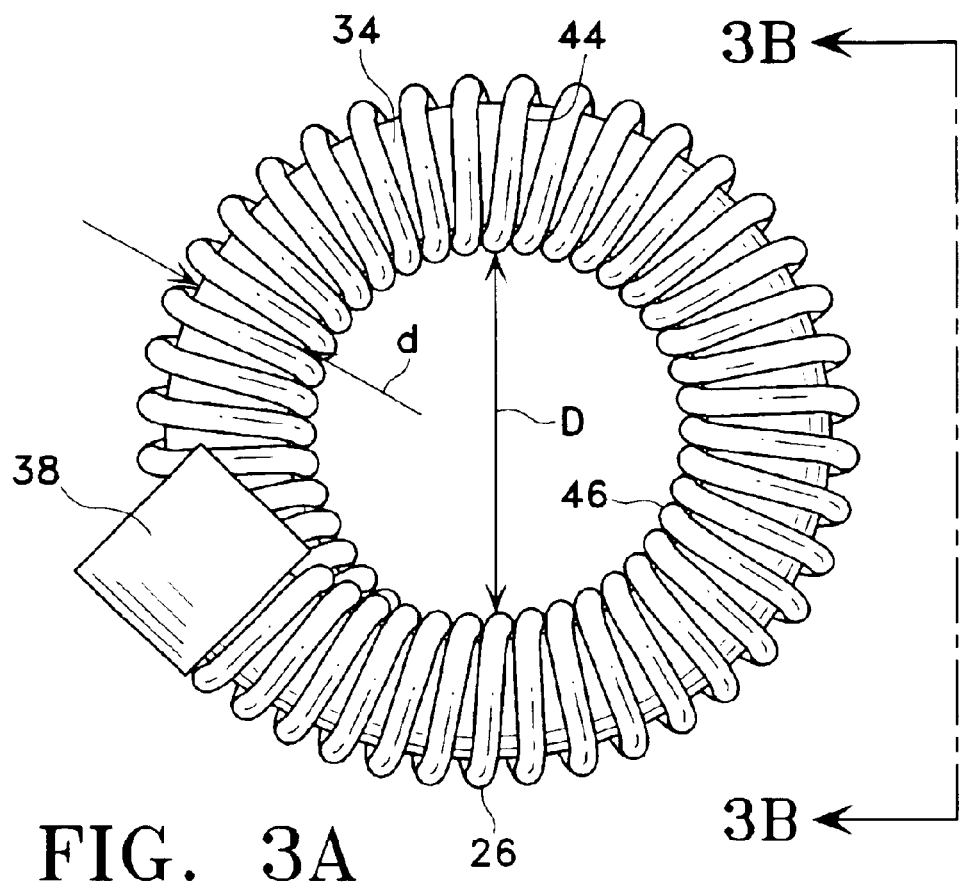
FIGS. 3A–3D are enlarged views of a fastener of the tissue connector assembly of FIG. 1, where

As shown in FIG. 3A, one embodiment of a fastener 10 comprises a deformable wire 34 made of a shape memory alloy. A nickel titanium (nitinol) based alloy may be used, for example. The nitinol may include additional elements which affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration. When the wire 34 is positioned within the tissue in its undeformed configuration, a residual stress is present to maintain the tissue tightly together (FIG. 2C). In order for the pseudoelastic wire 34 to retain sufficient compression force in its undeformed configuration, the wire should not be stressed past its yield point in its deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 8–10 degrees Celsius).

It is to be understood that the shape memory alloy may also be heat activated, or a combination of heat activation and pseudoelastic properties may be used, as is well known by those skilled in the art.

The cross-sectional diameter of the wire 34 and length of the wire will vary depending on the specific application. The diameter "d" of the wire 34 may be, for example, between 0.001 and 0.015 inch. For coronary bypass applications, the diameter is preferably between 0.001 and 0.008 inch with a diameter "D" of the loop being between 0.0125 and 0.0875 inch (FIG. 3A). The diameter "D" of the loop of the fastener 120 in its closed position is preferably sized to prevent movement between adjacent tissues. As shown in FIG. 3A, the wire 34 has a circular cross-sectional shape. It is to be understood that the wire may have other cross-sectional shapes such as rectangular, or may be formed from multiple strands without departing from the scope of the invention.

Figure 3B:
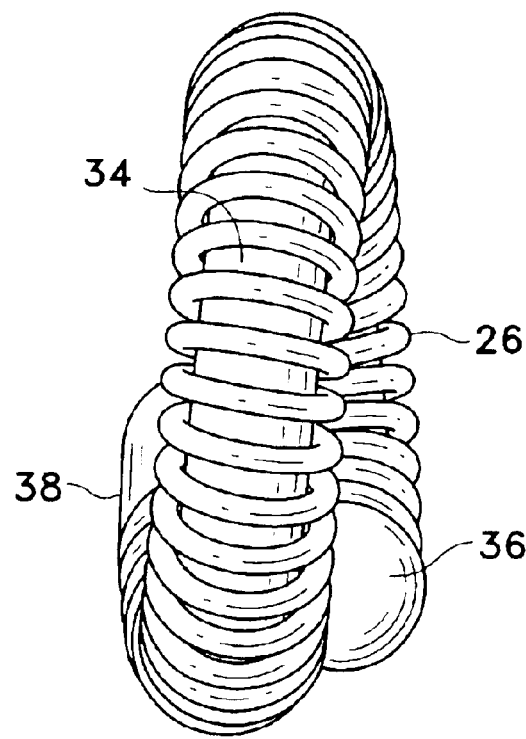
Figure 3C:
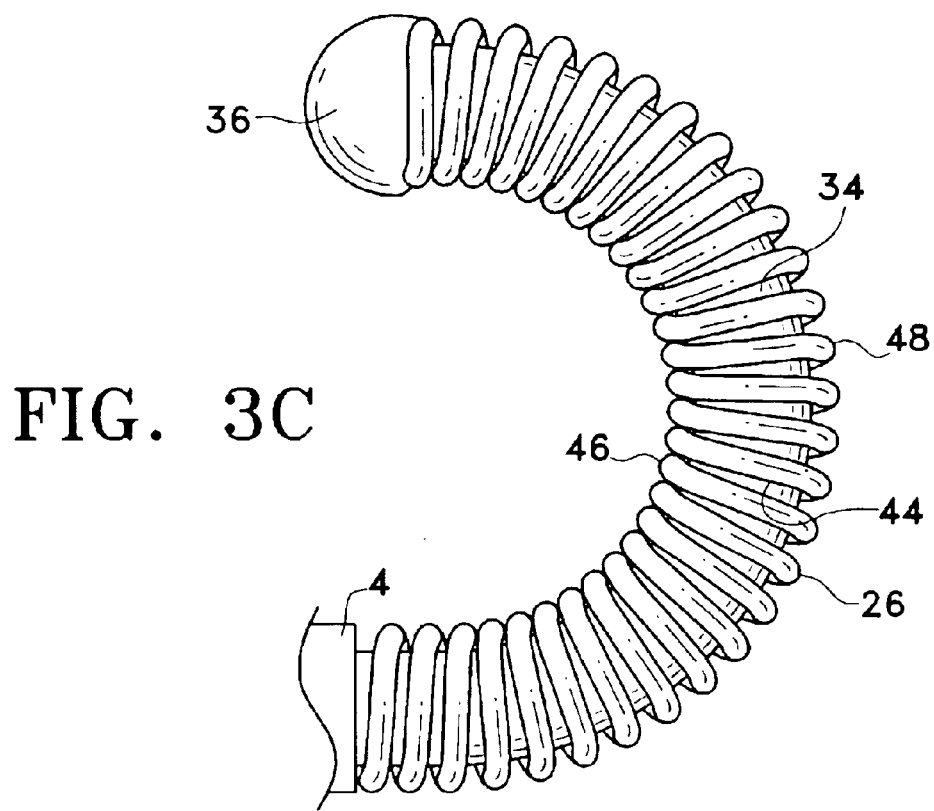

The proximal end of the wire 34 may include a stop 36 having a cross-sectional area greater than the cross-sectional area of the wire and coil 26 to prevent the wire and coil from passing through the tissue (FIG. 3C). The stop 36 may be attached to the end of the wire 34 by welding, gluing or other suitable attachment means or may be formed integrally with the wire by deforming the end of the wire. There are several embodiments of stop 36 that provide for different uses or applications of the inventive fasteners. Thus in one embodiment, the stop 36 may be large enough to prevent the proximal end of wire 34 from being pulled through the tissue. In another embodiment, the stop may provide coupling to additional flexible members or needles, as described below and in copending patent application Ser. No. 09/260, 623. In yet another embodiment, the stop 36 may be eliminated to facilitate pulling the fastener completely through the tissue, if, for example, the entire fastener needs to be removed from the vessel during the insertion procedure. The distal end of the wire 34 includes an enlarged portion 38 for engagement with one of the restraining devices 8 as further described below (restraining devices 8a in FIG. 4A and 8c in FIG. 12A), or other equivalent structures. The enlarged portion 38 may be formed by deforming the end of the wire 34 by swaging or arc welding, or attaching by welding, swaging, or other suitable means to form an enlarged portion at the end of the wire.

The wire 34 has an undeformed or closed position (state or configuration) for keeping or connecting tissue together, and a deformed or open position (state or configuration) for insertion of the wire into tissue, and is moved from its closed position to its open position by one of the restraining devices 8, as further described below. The wire 34 is preferably not deformed past its yield point in its open position. Accordingly, one embodiment provides a U-shaped configuration for an open position to facilitate insertion of the wire 34 through the tissue. It is to be understood that a U-shaped configuration may be alternatively substituted by an equivalent structure such as C-shaped, V-shaped, J-shaped, and other similarly shaped configurations. When in its closed position, the wire 34 of the first embodiment forms a loop with the ends of the wire in a generally side-by-side or overlapping orientation (FIG. 3B).

The wire 34 may be formed in the above described shape by first wrapping the wire onto a mandrel and heat treating the wire at approximately 400–500 degrees Celsius for approximately 5 to 30 minutes. The wire 34 is then air quenched at room temperature. The mandrel may have a constant diameter, may be conical in shape, or may have other shapes for treating a wire into a shape useful for producing a fastener.

Figure 3D:
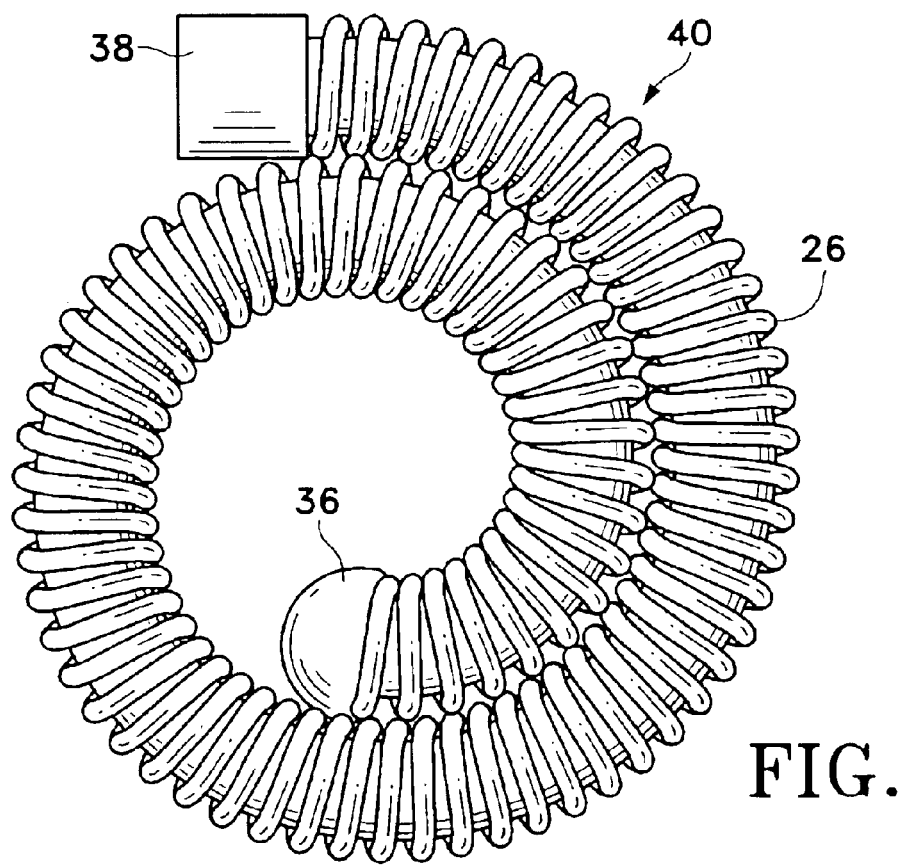

An alternate configuration of the surgical fastener 10 in its closed position is shown in FIG. 3D, and generally indicated at 40. The fastener 40 forms a spiral configuration in its closed position for trapping tissue within a loop formed by the spiral. In its open position, the fastener 40 is configured to form less than a full 360 degree turn.

Figure 3E:
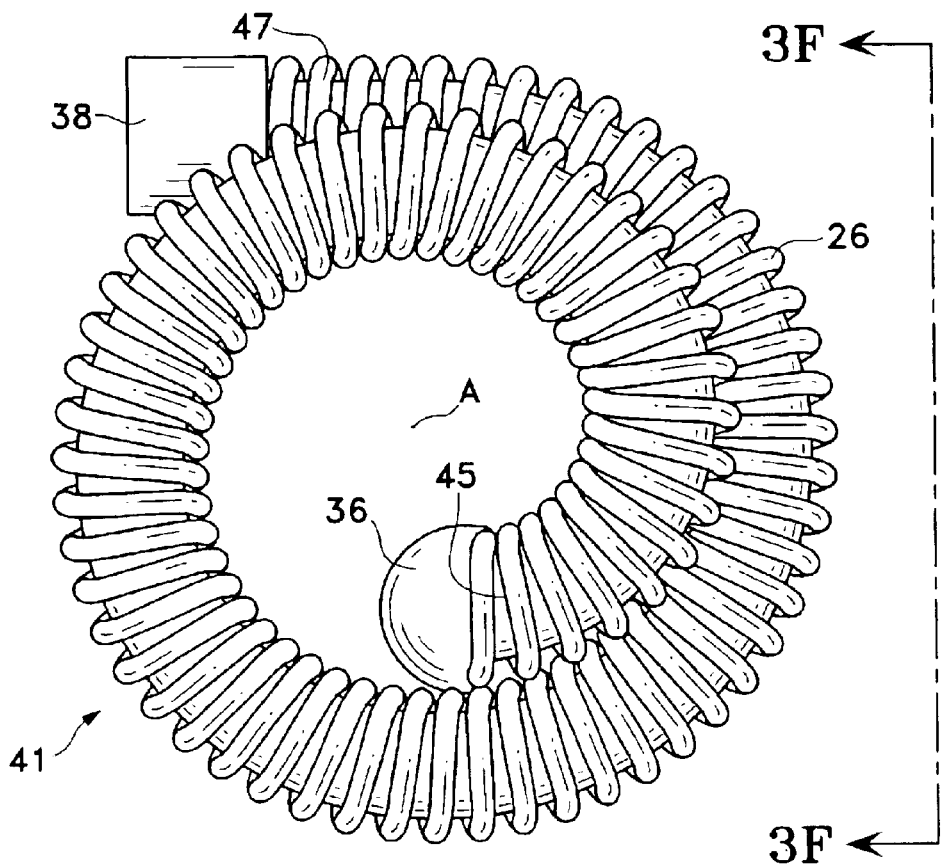
FIGS. 3E–3G are enlarged views of an alternate configuration of the fastener of the tissue connector assembly of FIG. 1, where
Figure 3F:
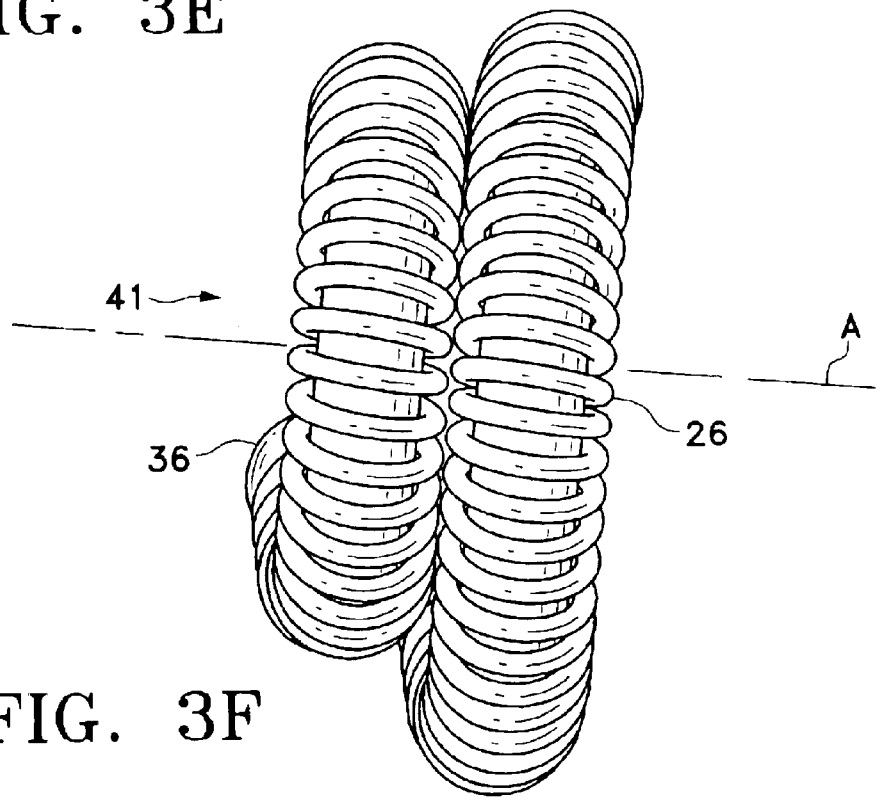

Another alternate configuration of the surgical fastener 10 is shown in FIGS. 3E and 3F in its closed position, and is generally indicated at 41. The fastener 41 is formed in a spiral about a central longitudinal axis A. As shown in FIG. 3F, the fastener 41 has a generally conical shape along the longitudinal axis A, with a decreasing diameter as the radius of curvature of the fastener 41 decreases. The fastener 41 has an inner end portion 45 and an outer end portion 47, with the enlarged portion 38 of the wire being disposed at the outer end portion for engagement with one of the restraining devices 8.

Figure 3G:
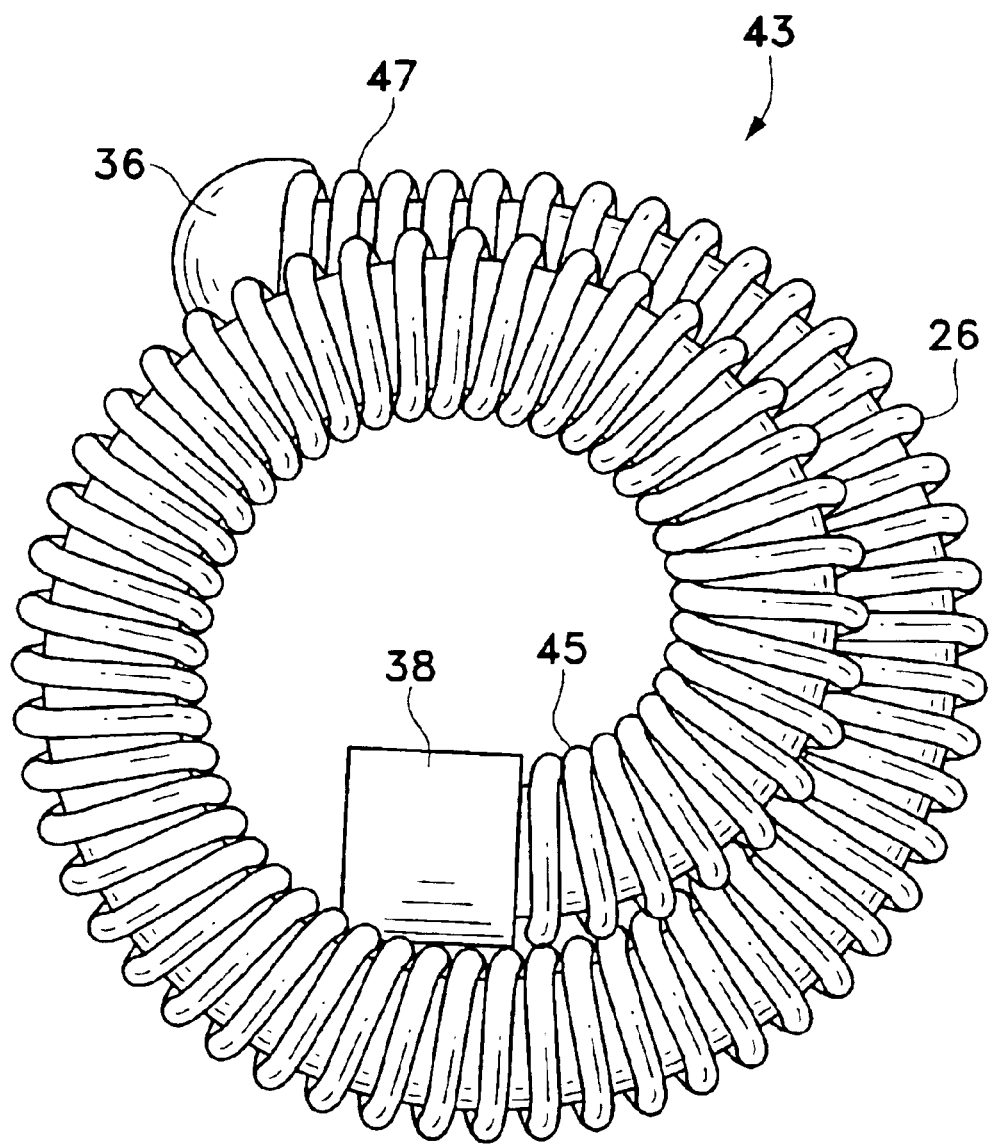

A modification of the fastener is shown in FIG. 3G, and generally indicated at 43. The fastener 43 is same as the fastener 41 described above, except that the enlarged portion 38, which is adapted for engaging a restraining device or releasable mechanism, is positioned at the inner end portion 45 of the fastener. Placement of one of the restraining devices 8 at the inner end portion 45 of the fastener 43 increases the compression force of the wire in its undeformed position on the tissue and decreases the surface area of the fastener exposed to blood flow.

Figure 11:
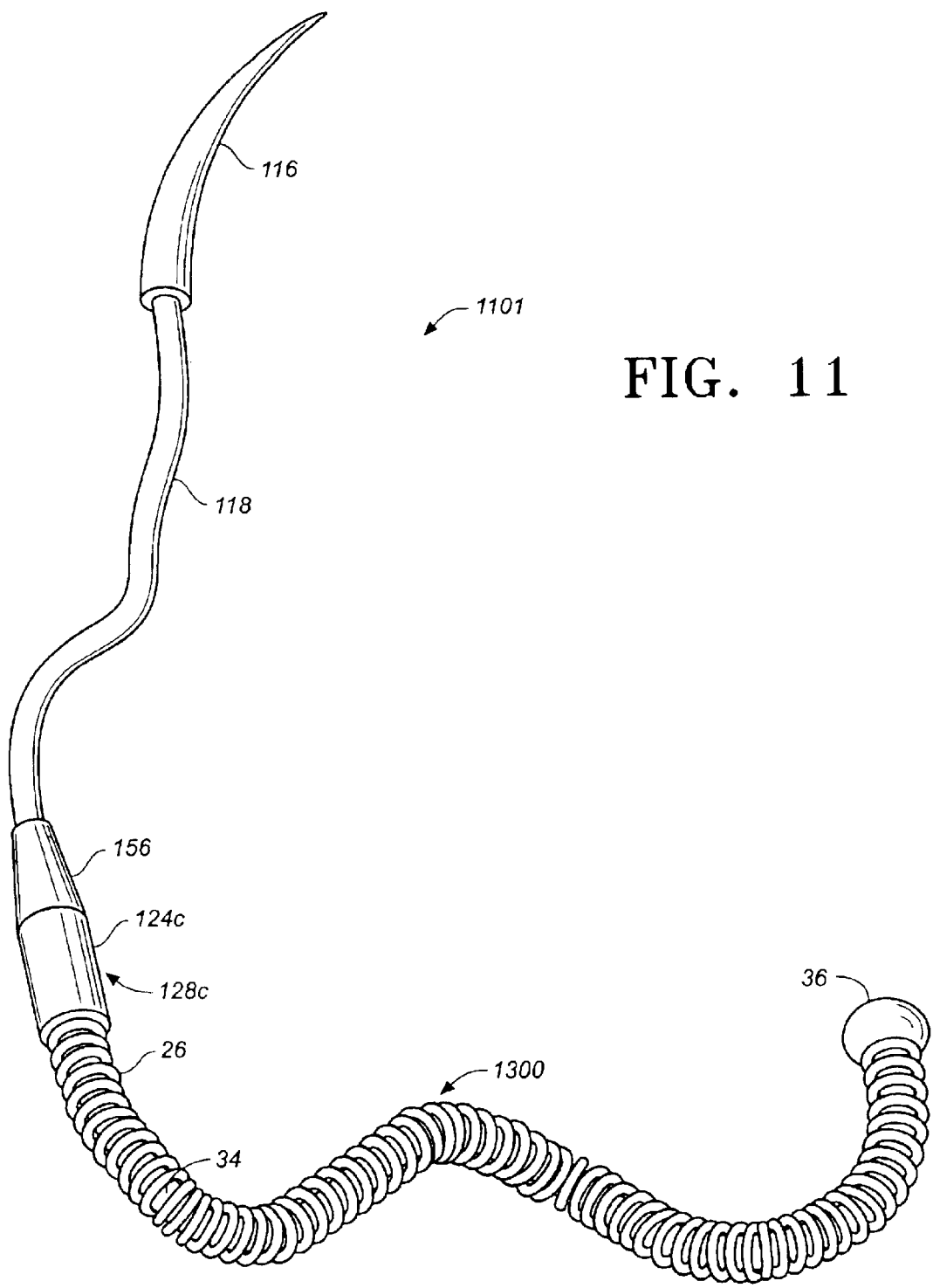
FIG. 11 is a front view of a single-arm tissue connector assembly having a multiple loop fastener of the present invention.
Figures 13A, 13C:
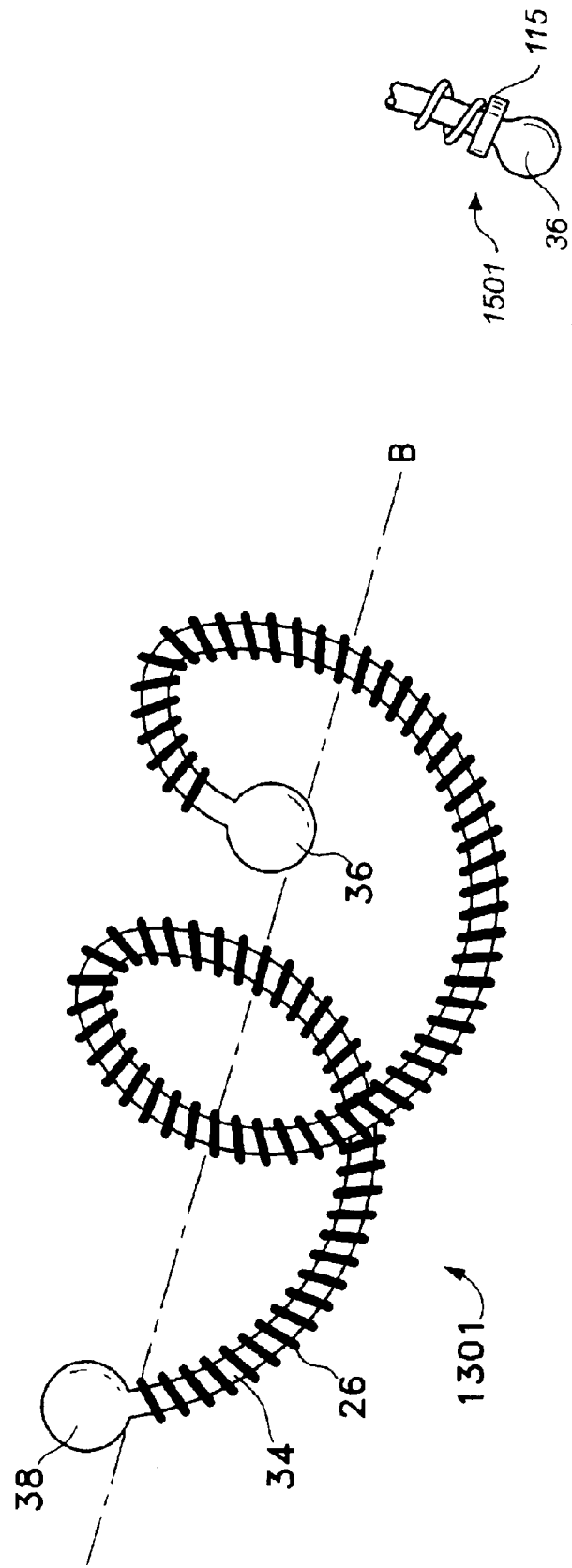
FIG. 13A–13D are front views of four alternate multiple loop fastener embodiments of the present invention in the closed configuration, where FIG. 13A has evenly spaced loops, FIG. 13B includes both evenly and unevenly spaced loops, and FIGS. 13C and D are details of fasteners of FIG. 13A and B, respectively, configured for use in a double-arm tissue connector assembly.
Figure 13B:
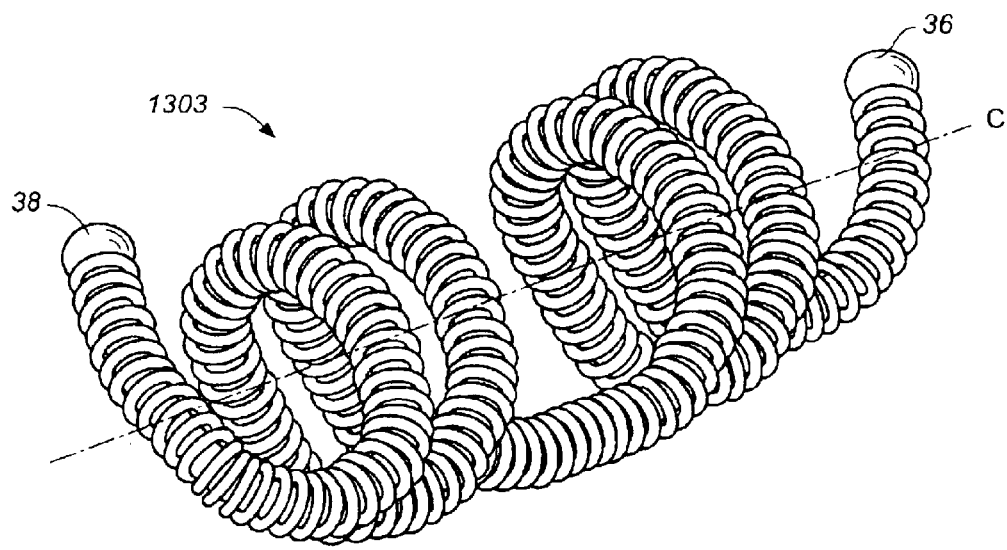

A second embodiment of wire 34, as shown in an open configuration in FIG. 11 and in a closed configuration in FIGS. 13A–13B. Specifically, FIG. 11 shows a front view of a single-arm tissue connector assembly 1101 having a multiple loop fastener in an open configuration, and generally indicated as 1300. FIG. 13A shows a particular multiple loop fastener 1301 having evenly spaced loops in a closed configuration, and FIG. 13B shows another particular multiple loop fastener 1303 having both evenly and unevenly spaced loops in a closed configuration. The multiple loop fasteners 1301 and 1303 are similar to the previously described fasteners 10, 40, 41, and 43, with the wire 34 specifically preformed as a spiral of more than one loop.

As shown if FIG. 13A, the loops of fastener 1301 are helical with a centerline B, and form slightly less than two complete loops. The enlarged portion 36 is preferably large enough to prevent coil 26 from moving off the proximal end of wire 34. In one embodiment, the distal end of wire 34 is configured to be threaded through a tissue, and the enlarged portion 36 is large enough to prevent the proximal end of wire 34 from being pulled through the tissue. As shown in FIG. 13B is the multiple loop fastener 1300 having both evenly and unevenly spaced loops, and generally indicated at 1303. The loops of fastener 1303 are formed on the surface on a cylinder having a centerline C. As with fastener 1301, the enlarged portion 36 is preferably large enough to prevent coil 26 from moving off the proximal end of wire 34. Also, as with fastener 1301, the distal end of wire 34 may be configured for threading through a tissue, with the enlarged portion 36 large enough to prevent the proximal end of wire 34 from being pulled through the tissue.

It is to be understood that the fastener 10, 40, 41, 43, 1300 and other fasteners described herein may have undeformed or deformed configurations different than those shown herein without departing from the scope of the invention. In addition, a locking clip (not shown) may also be attached to connect the ends of the fasteners of this invention when the fastener is in its closed position to prevent possible opening of the fastener over time. The locking clip may also be integrally formed with one end of the fastener.

The wire 34 of any of the fasteners of the present invention, as shown for example in FIG. 3A–3C, may be surrounded by the spring or coil 26 which, along with the locking device 4a, restrains the wire in its deformed configuration. The coil 26 comprises a helical wire forming a plurality of loops which define a longitudinal opening 44 for receiving the shape memory alloy wire 34. The coil 26 may be formed from a platinum alloy wire having a cross-sectional diameter of approximately 0.0005–0.005 inch, for example. The wire may have other cross-sectional shapes and be formed of different materials. The coil 26 is preferably sized so that when in its free (uncompressed state) it extends the length of the wire 34 with one end adjacent the stop 36 at the proximal end of the wire and the other end adjacent the enlarged portion 38 at the distal end of the wire (FIG. 3B). It is to be understood that the spring 26 may not extend the full length of the wire. For example, a flange or similar device may be provided on an intermediate portion of the wire 34 to limit movement of the coil along the length of the wire.

When the coil 26 is in its free state (with the wire 34 in its undeformed configuration), loops of the coil are generally spaced from one another and do not exert any significant force on the wire 34 (FIG. 3A). When the coil 26 is compressed (with the wire 34 in its deformed configuration), loops of the coil on the inner portion 46 of the coil are squeezed together with a tight pitch so that the loops are near or contiguous with one another while loops on the outer portion 48 of the coil are spaced from one another (FIG. 3C). This is due to the compressed inner arc length of the coil 26 and the expanded outer arc length of the coil. The compression of the loops on the inner portion 46 of the coil 26 exerts a force on the inner side of the wire 34 which forces the wire to spread open (i.e., tends to straighten the wire from its closed configuration to its open configuration). The end of the coil 26 adjacent the stop 36 is held in a fixed position relative to the wire 34. The opposite end of the coil 26 is free to move along the wire 34 and is held in place when the coil is in its compressed position by the locking device 4a (FIG. 4A).

The locking device 4a shown in FIGS. 4A–4C comprises a flexible tubular member 50 having a distal end portion 52 coupled to a needle 2 and a proximal end portion 54 releasably attached to the wire 34. The tubular member 50 is movable between a locked position (FIG. 4A) for holding the coil 26 in its compressed position and the wire 34 in its deformed position, and an unlocked position (FIG. 4C) for inserting or releasing the wire and coil. Three slots 58 are formed in the tubular member 50 extending from the proximal end 54 of the member and along at least a portion of the member (FIGS. 4B and 4C). The slots 58 are provided to allow the proximal end 54 of the tubular member 50 to open for insertion and removal of the wire 34 when the tubular member is in its unlocked position (FIG. 4C). It is to be understood that the number of slots 58 and configuration of the slots may vary.

The proximal end 54 of the tubular member 50 includes a bore 62 having a diameter slightly greater than the outer diameter d of the wire 34, but smaller than the diameter of the enlarged portion 38, and smaller than the outer diameter of the coil 26. The bore 62 extends into a cavity 64 sized for receiving the enlarged portion 38 of the wire 34. Member 50 may be described as having an annular flange 61 for releasably securing the enlarged portion 38. As shown in FIG. 4C, upon application of an inwardly directed radial squeezing force on the tubular member 50 the proximal end 54 of the tubular member is opened to allow for insertion or removal of the wire 34. When the force is released (FIG. 4A), the tubular member 50 moves back to its locked position and securely holds the wire 34 in place and compresses the coil 26. A disc 51 may be inserted into the tubular member 50 to act as a fulcrum and cause the proximal end 54 of the tubular member to open upon application of force on the tubular member. Alternatively, the disc 51 may be integrally formed with the tubular member 50. As shown in FIG. 4A, the length 1 of the bore 62 or flange 61 determines the amount of compression of the coil, which in turn determines the amount of deformation of the wire 34. The greater the length 1 of the bore 62, the greater the compression of the coil 26 and the more straightening the wire 34 will undergo. The compression of the coil 26 is preferably limited so that the wire 34 is not stressed beyond its yield point. This allows the wire 34 to revert back to its original undeformed configuration and apply sufficient pressure to hold the connected tissue together.

Figure 5:
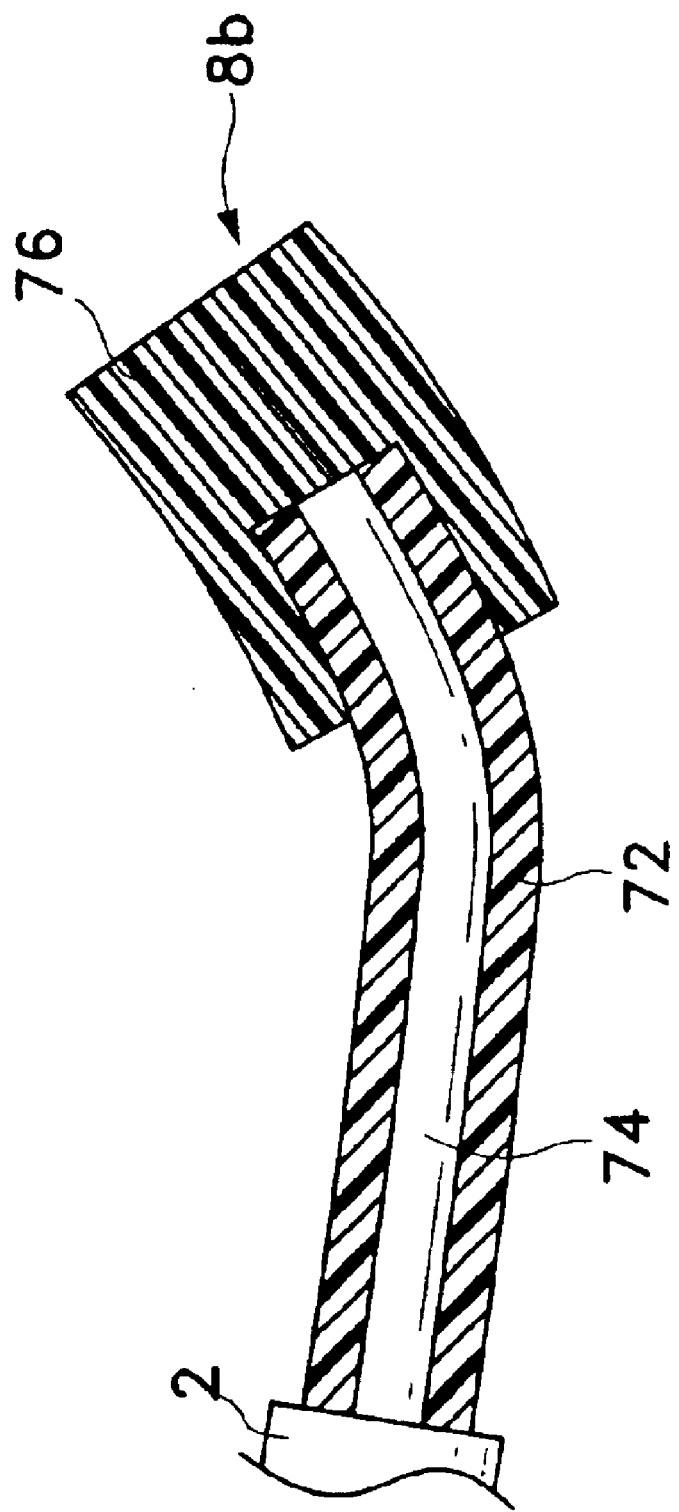
FIG. 5 is an alternate embodiment of the restraining device of FIG. 4A.

An alternate embodiment of the restraining device is shown in FIG. 5, and generally indicated with reference numeral 8b. The restraining device 8b is used with a tubular (hollow) shape memory alloy wire or tube 72 and comprises an elongated member (or mandrel) 74 sized for insertion into the wire. The mandrel 74 is preferably formed from a material which is stiffer than the material of the wire 72 so that upon insertion of the mandrel into the wire, the wire is deformed into its open position. The restraining device 8b includes a stop 76 located at the proximal end of the wire 72. The stop operates to prevent the fastener from being pulled through the tissue, and limits axial movement of the mandrel 74 in the proximal direction (to the right as viewed in FIG. 5). The distal end of the mandrel 74 is releasably attached to the needle 2.

Figure 12D:
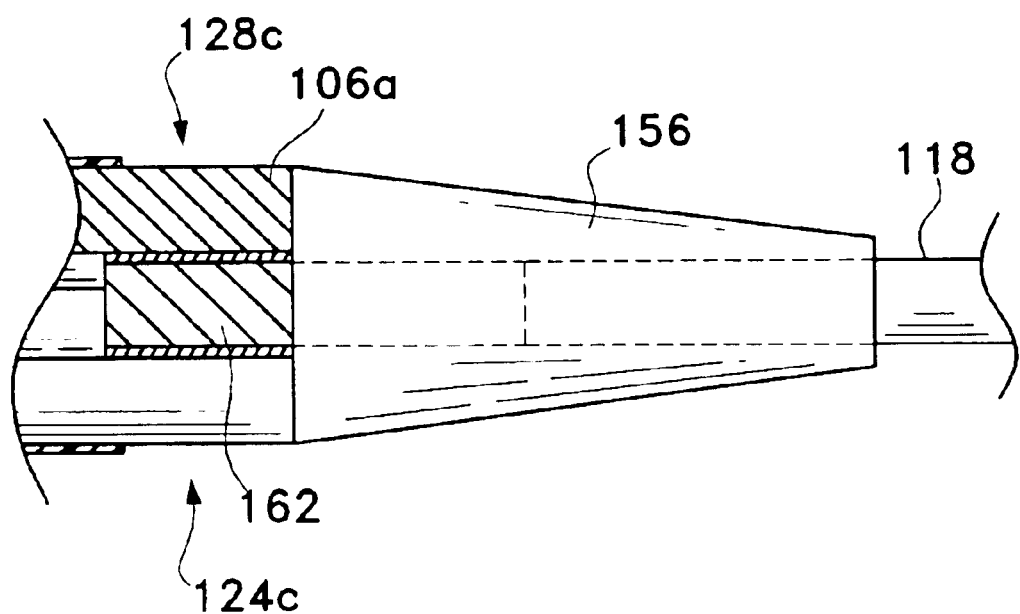

Yet another alternate embodiment of the restraining device, generally indicated with reference numeral 8c, and locking device, generally indicated with reference numeral 4c, is shown in FIG. 12. Specifically, FIGS. 12A–12E illustrate a release mechanism or restraining device which is disclosed in U.S. patent application Ser. No. 09/259,705, filed on Mar. 1, 1999 and entitled Tissue Connector Apparatus With Cable Release. FIGS. 12A–C show the mechanism coupled with a fastener, and FIGS. 12D and 12E show the release mechanism depressed for release of the fastener. Restraining device 8c comprises a plurality of substantially rigid strands, preferably wires 106, arranged substantially parallel to one another and circularly about a longitudinal axis of the aligned strands, to form a tube-like configuration, as can be seen in the cross-sectional view of FIG. 12C and the perspective view in FIG. 12A. Restraining device 8c has a distal end portion 106a that can be coupled to needle 2 and a proximal end portion 106b releasably attached to the wire 34. Alternatively, strands 106 may be cables or some other substantially rigid strand elements arranged in the same manner as the wires shown in FIG. 12C.

Preferably, a rod 162 extends into distal end portion 106a to facilitate fixation of the strands thereto, as shown in FIG. 12B. The coupling of the strands to needle 2 is preferably accomplished by gluing or soldering to rod 162, although other equivalent or similar known joining techniques may be employed (e.g. welding, threadably attaching, etc).

Similarly, rod 162 is preferably glued, soldered or threaded into the needle.

The end portions 106b of the strands in the vicinity of the fastener strands include notches 109 which are formed into the strands to a depth equal to approximately half the diameter of the strand 106. When the strands are arranged in the circular configuration described above, the notches 109 form a chamber 108 configured for receiving and holding enlarged portion 38. Although enlarged portion 38 is shown as having a spherical shape, it may have other shapes including a barrel shape, or other shape that may be easily grasped and easily released. The notches are preferably placed about 0.015" from the free ends of the strands, but this distance, of course, can be modified, depending upon the amount of compression of spring 26 that is desired when ball 38 is inserted into and held by notches 109.

After placement of ball 38 within chamber 108 formed by notches 109, a shrink wrap layer, preferably a shrink tubing 105 may be provided over at least free end portions 106b of wires or strands 106, and the tubing heated to compress against strands 106 and hold them in place against ball 38, preferably symmetrically against ball 38. Together, tubing 105 and strands 106 effectively hold ball 38 captive within notches 109, acting as locking mechanism 4. Alternatively, other plastic or elastic restraining members may be mounted around the distal portions of the wires or strands to aid in maintaining them in place, preferably symmetrically against ball 38. Still further, strand members may be designed with an elastic spring force sufficient to maintain notches 109 in place with sufficient force to maintain the ball 38 captive therein under the tensile forces normally experienced during a suturing procedure. Although a seven-strand embodiment is shown, it should be understood that fewer or more than seven strands may be used. The number of strands may vary depending on, for example, the size of the fastener or the size of the strands. Typically, the number of strands may range from two to ten. In a coronary anastomosis, the number of strands preferably will range from five to seven although other numbers may be used.

In assembling, enlarged portion 38 of vire 34 is placed in chamber 108. Tubing 105 is wrapped around at least a portion of the strands (as shown in the drawings) and heated to maintain enlarged portion 38 captive within the cavity formed by the strands. Compression coil or spring 26 is slid over wire 34 and compressed against portions 106b such that the fastener is in its open configuration. Enlarged portion 36 may then be formed or attached to wire 34 to maintain the fastener in its open configuration.

Locking device 4c is movable between a locked position (FIGS. 12A–12C) and an unlocked position (FIGS. 12E and 12F). In the locked position the ball 38 is held within notches 109 and consequently, coil 26 is held in its compressed position, thereby maintaining fastener wire 34 in its deformed or open position. In the unlocked position, ball 38 is released from the notches, thereby allowing the coil 26 to expand, which causes the fastener wire 34 to close. The closure conformation of the wire may be characterized by any of those described above with reference to FIG. 3 or the subsequently described FIGS. 13, for example.

Movement of the locking mechanisms 4c, and thus release of restraining device 8c, to the open position is accomplished by applying a compressive force to the shrink tube 105 and bundle of strands 106, as shown in FIGS. 12E and 12F. Advantageously, the compressive force may be applied at any opposing locations around the circumference of the shrink tube as long as the implement applying the force is oriented at an angle to the strands, preferably substantially perpendicular thereto, to allow the implement to traverse the strands so as to deform the positions thereof when the force is applied. For example, needle holder 111 could be rotated 90° (or virtually any other angle) with respect to the strands 106 as shown in the plane of the drawing, while retaining the capability of deforming the strands to an open position upon application of a compressive force. The compressive force is preferably applied using a standard needle holder 111 or forceps, although other tools could be used, preferably those with applicators narrower than the length of the shrink tube 105. As shown, the strands or wires 106 get distorted from their circular configuration under the compression. This change in shape stretches the shrink tube 105 from a circular configuration to a somewhat elliptical configuration, and removes some of the notches 109 from contact with ball 38, thereby permitting removal of ball 38 from within the chamber previously formed by notches 109 in the closed position. It is to be understood that in addition to the restraining devices disclosed herein, other types of restraining devices may be used without departing from the scope of the invention.

It is to be understood that locking devices other than those described above may be used without departing from the scope of the invention. For example, a locking device (not shown) may comprise a tubular member having an opening formed in a sidewall thereof for receiving an end portion of the wire. The end of the wire may be bent so that it is biased to fit within the opening in the sidewall of the tubular member. An instrument, such as a needle holder may then be used to push the wire away from the opening in the tubular member and release the wire from the tubular member. Various other types of locking devices including a spring detent or bayonet type of device may also be used.

Another embodiment of the tissue connector assembly is shown in FIG. 6 and generally indicated with reference numeral 110. The tissue connector assembly 110 is similar to the tissue connector assembly 1 of the first embodiment, except that a flexible member 118 is inserted between a restraining device 124a and needle 116. FIG. 6 shows the tissue connector assembly 110 with a fastener 120 in an open (deformed) position. The fastener 120 may be the same as the fasteners 10, 40, 41, 43 described above and shown in FIGS. 3A–3G for the tissue connector assembly 1 of the first embodiment, for example. The fastener 120 includes the restraining device 124a comprising a coil 126 and a locking device 128a. The locking device 128a and the restraining device 124a are similar to those described above and shown in FIGS. 4A–4C, except that the distal end is configured for attachment to the flexible member 118. An alternative locking device 128c and a restraining device 124c, similar to those described in FIGS. 12A–12C, are shown attached to the flexible member 118.

The flexible member 118 is attached to the distal end of the locking device 128 with a tapered portion or transition sleeve 156 extending from the locking device to the flexible member 118 to facilitate insertion of the locking device through tissue. The tapered sleeve 156 is preferably sufficiently curved to facilitate movement of the tissue connector assembly 110 through connecting tissue in an anastomosis, for example. The sleeve 156 may be formed from a metal alloy such as stainless steel or a suitable polymeric material. The needle 116 may be swaged into the sleeve 156, or a heat shrink plastic covering may hold the needle in place. The locking device 128 may also be curved.

The flexible member 118 may be in the form of a suture formed from conventional filament material, metal alloy such as nitinol, polymeric material, or any other suitable material. The material may be non-stretchable or stretchable, solid or hollow, and have various cross-sectional diameters. The suture may have a cross-sectional diameter of 0.003 inch, for example. The diameter and length of the suture will vary depending on the specific application. The suture may be attached to the needle 116 by crimping or swaging the needle onto the suture, gluing the suture to the needle, or any other suitable attachment method. The flexible member 118 may have cross-sectional shapes other than the one shown herein.

The needle 116 may be integrally formed with the flexible member 118. The diameter of at least a portion of the needle 116 is preferably greater than the diameter of the flexible member 118 so that the flexible member can easily be pulled through an opening formed in the tissue by the needle.

Another embodiment of the tissue connector assembly is shown in FIG. 11, and generally indicated with reference numeral 1101. FIG. 11 shows the tissue connector assembly 1101 with a fastener 1300 in an open (deformed) position. The tissue connector assembly 1101 is similar to the tissue connector assembly 110, the major difference being the attachment of a multiple loop fastener 1300 to flexible member 118. The loops may be helical, spiral, or have other looping shapes, including variations in loop shape from loop-to-loop and changes in shape along the loop to aid in the clipping functions discussed subsequently. The loops may also have bends or turns at the wire 34 ends. FIG. 11 shows the tissue connector assembly 1101 with a fastener 1300 in an open (deformed) position. The fastener 1300 includes the restraining device 124c comprising a coil 26 and a locking device 128c. The transition from the distal end portion 106a of restraining device 124c is shown in FIG. 12D. Alternatively, the restraining device 124a and locking device 128a could be substituted for those in the embodiment of FIG. 11.

Figure 15:
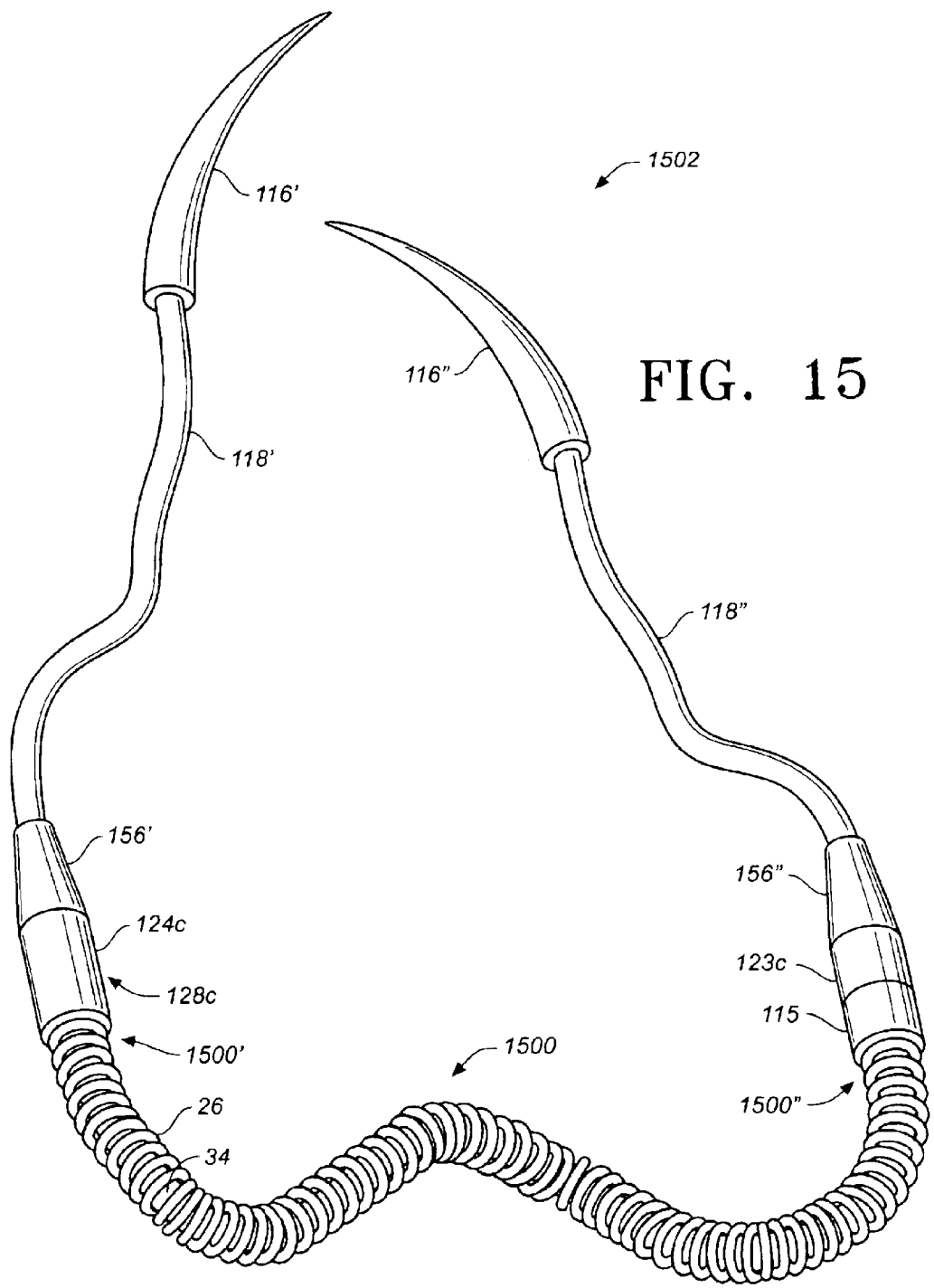
FIG. 15 is a front view of a double-arm tissue connector assembly having a multiple loop fastener of the present invention.

Yet another embodiment of the tissue connector assembly is shown in FIG. 15 as a double-arm tissue connector assembly, and generally indicated with reference numeral 1502. The double-arm tissue connector assembly 1502 is a double-arm assembly, in which a multiple loop fastener 1506 is attached to two needles, 116' and 116". Previous disclosure of a double-arm assembly attached to fasteners such as fastener 10, 40, 41, 43 has been disclosed in copending patent application Ser. No. 09/260,623, filed Mar. 1, 1999, of which this application is a continuation-in-part.

Figure 16G:
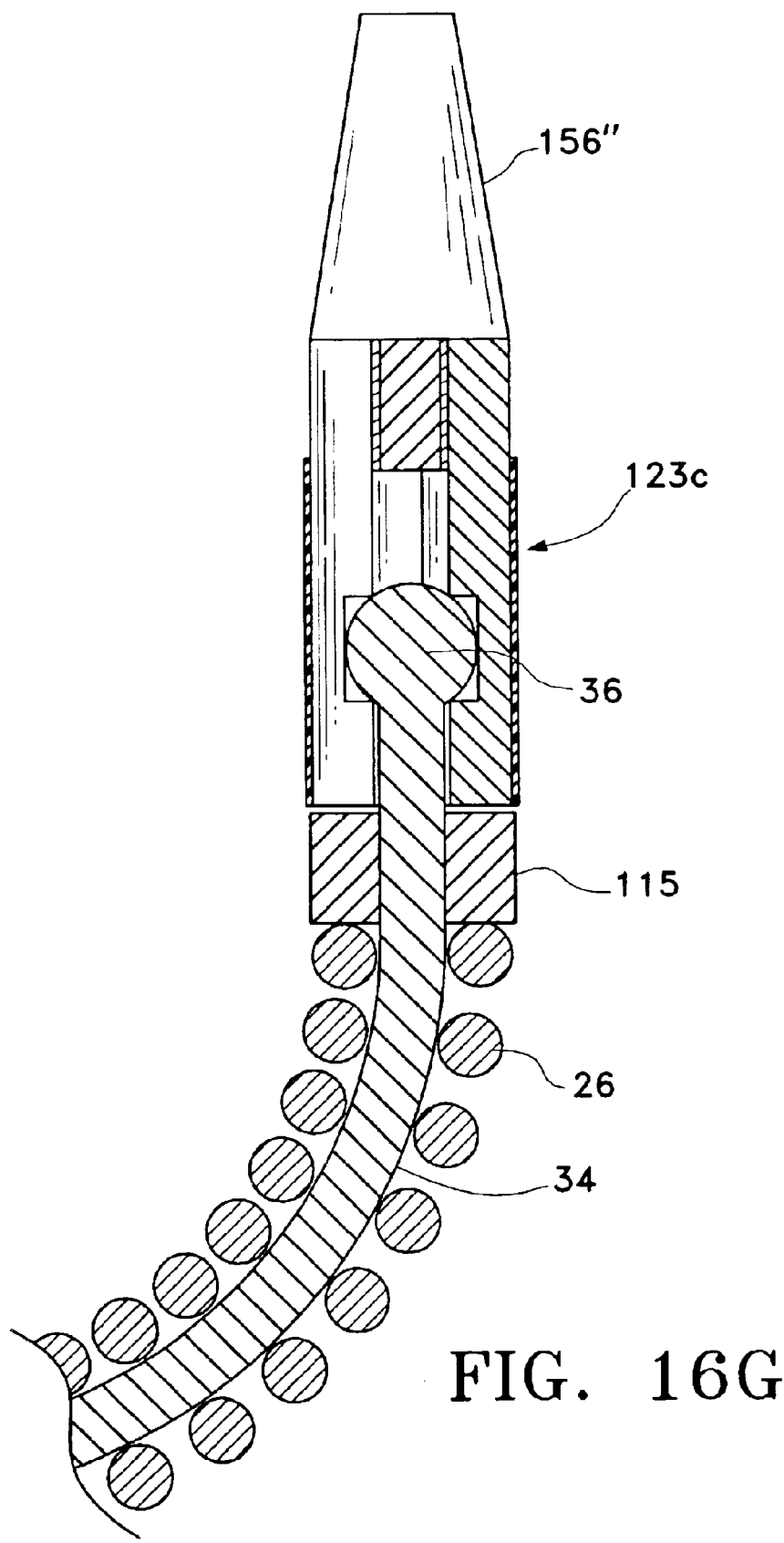
FIG. 16G shows yet another synchronized fastener release system in the coupled state for use on a double-arm tissue connector as in FIG. 15.

In the embodiment of FIG. 15, a multiple loop fastener 1500 has two ends adapted to be connected to and released from a corresponding needle. A first fastener end 1500' has restraining device 124c and locking mechanism 128c, as in the distal end of the fasteners previously described for single needle use. The first fastener end 1500' is attached to first needle 116' through a first flexible member, such as flexible member 118', which in turn is coupled to needle 116'. A second fastener end 1500" is attached to second needle 116" through a flexible member such as second flexible member 118". The second fastener end 1500" has a release mechanism 123c for releasably coupling fastener 1500 to flexible member 118", as shown in FIG. 16G. In this arrangement, a member or stopper 115, which may be annular, is secured to the other end of the fastener or wire 34 to prevent enlarged portion 36 from passing through the compression spring upon release from release mechanism 123c. This arrangement thus allows for the activation of locking mechanism 128c to release both flexible members 118' and 118" from fastener 1500.

Figure 13D:
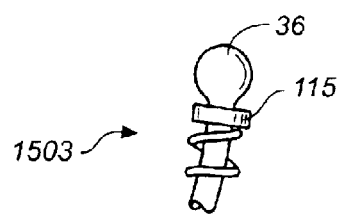

Examples of double-arm fasteners are shown in FIGS. 13A–13D. Specifically, where FIG. 13A has evenly spaced loops, FIG. 13B includes both evenly and unevenly spaced loops, and FIGS. 13C and D are details of fasteners of FIG. 13A and B, respectively, configured for use in a double-arm tissue connector assembly. Fastener 1501 of FIG. 13C and fastener 1503 of FIG. 13D are modified versions of fasteners 1301 and 1303, respectively, where the enlarged end 36 has been modified to work with release mechanism 123c, as in FIG. 16G. Thus FIG. 13C shows an evenly spaced loop, as in FIG. 13A, where a stopper 115 has been added to the enlarged portion end 36, and FIG. 13D shows a combined evenly and unevenly spaced loop fastener with the enlarged portion suitably modified.

Other combined release and restraining mechanisms, which provide synchronized release of both needles illustrated in FIG. 15, also can be used. FIGS. 16A–16F illustrate synchronized fastener release systems. Referring to FIGS. 16A–16C, a first synchronized release system is shown in a coupled and decoupled state, respectfully. Although one release mechanism is shown as corresponding to restraining device 128c and locking device 124c, any release mechanism which releasably couples the flexible member or needle to the surgical fastener and effects compression of coil 26 also may be used. At the other end of the fastener or wire 34, a release mechanism that responds to the compressive state of coil 26 and releases the fastener or wire 34 upon release of compressive forces on the coil is shown and generally designated with reference numeral 123a. Release mechanism 123a comprises two members 1601 each having a recess 122 formed therein and arranged to form chamber 1603 when members 1601 are aligned as shown in FIG. 16A. Recesses 122 are configured to retain enlarged portion 36, which is shown with a cylindrical configuration, but may have a spherical or other suitable shape for operatively associating with a suitably configured chamber. Further, members 1601 may have semicircular transverse cross sections or some other combination of transverse shapes that can collectively provide the desired chamber to retain enlarged portion 36. The number of members 1601 also may vary as would be apparent to one of ordinary skill.

Restraining device members 1601 have tapered ends 1605, which are configured for positioning between coil 26 and fastener wire 34 as shown in FIG. 16A. When tapered ends 1605 are so positioned and coil 26 is in a compressed state, coil 26 holds tapered ends 1605, which are normally biased away from each other as shown in FIG. 16C, sufficiently together to retain enlarged portion 36 within chamber 1603. When locking device 128c is actuated (e.g., radially compressed to release enlarged portion 38 of fastener wire 34, coil 26 assumes its relaxed state, thereby releasing tapered ends 1605 of release mechanism 123a from the coil and allowing the tapered ends to radially expand and release enlarged portion 36 of fastener wire 34 as shown in FIG. 16C. Accordingly, both needles and flexible members may be decoupled from the fastener when restraining device 123a is actuated.

FIGS. 16D–16F show another synchronized fastener system that is the same as the system shown in FIGS. 16A–16C with the exception of release mechanism 123b and the cooperating portion of the fastener or wire 34 being substituted for release mechanism 123a. In this embodiment, an annular member or stopper 115, which may be annular, is slidably coupled to fastener wire 34. Member 115 is configured to resist passage of coil 26 thereover. Accordingly, member 115 may have an outer diameter slightly greater than at least the portion of the coil adjacent thereto. A tapered or frustoconical member 156''' is secured to an end of fastener wire 34, which need not include an enlarged portion. Member 156''' is the same as member 156'' with the exception that member 156''' has a channel 134 for receiving flexible member or suture 118''. Channel 134 extends radially outward from bore 132, which is formed through member 156''', for receiving the fastener or wire 34.

Flexible member 118'' is threaded through channel 134 and between tapered member 156''' and annular member 115. When coil 26 is in a compressed state as shown in FIG. 16D, the coil urges member 115 toward tapered member 156''' and compresses flexible member 118'' therebetween. In this manner, flexible member 118'' is secured to the fastener or wire 34. When locking device 128c is actuated (e.g., radially compressed) to release enlarged portion 38 of the fastener or wire 34, coil 26 assumes its relaxed state so that annular member 155 may slide away from tapered member 156''' and release flexible member 118''. Accordingly, both needles and flexible members may be removed from the fastener when locking device 128c is actuated. Although a metal flexible member may be used, a polymeric flexible member may be preferred.

As noted above, the tissue connector assemblies 1, 110, 1101, and 1502 of this invention have many uses. They may be especially useful in minimally invasive surgical procedures including creating an anastomosis between vascular graft 12 and artery 14 (FIGS. 2A–2C). The anastomosis may be used to replace or bypass a diseased, occluded or injured artery. A coronary bypass graft procedure requires that a source of arterial blood flow be prepared for subsequent bypass connection to a diseased artery. An arterial graft may be used to provide a source of blood flow, or a free graft may be used and connected at the proximal end to a source of blood flow. Preferably, the source of blood flow is one of any number of existing arteries which may be dissected in preparation for the bypass graft procedure. In many instances it is preferred to use the left internal mammary artery (LIMA) or the right internal mammary artery (RIMA), for example. Other vessels which may be used include the saphenous vein, gastroepiploic artery in the abdomen, radial artery, and other arteries harvested from the patient's body as well as synthetic graft materials, such as DACRON® or GORETEX® (expanded polytetrafluoroethylene). If a free graft vessel is used, the upstream end of the dissected vessel, which is the arterial blood source, will be secured to the aorta to provide the desired bypass blood flow, as is well known by those skilled in the art. The downstream end of the graft vessel is trimmed for attachment to an artery, such as the left anterior descending coronary (LAD). It is to be understood that the anastomosis may be formed in other vessels or tissue.

In addition, assemblies providing multiple loop fasteners, such as assemblies 1101 and 1502, allow for forming more than one stitch per fastener. Tissue secured with a multiple stitch, self-closing fastener has many advantages over conventional suture. For example, it allows for a greater are of tissue to be connected per time. In addition, multiple loop fasteners 1300 or 1500 are more rigid and can be formed to provide a greater closing force on the tissue than can be provided by conventional suture.

FIGS. 2A–2C and 7–9 show an exemplary use of the tissue connector assemblies 1, 110 for connecting graft vessel 12 to artery 14 (target vessel). In this example, two tissue connector assemblies 110 (FIG. 6) are used to make connections at generally opposite sides of the graft vessel and a plurality of tissue connector assemblies 1 (FIG. 1) are used to make connections between those made with tissue connector assemblies 110. The procedure may be accomplished with a beating heart procedure with the use of a heart stabilizer to keep the heart stable, for example. The procedure may also be performed endoscopically.

Figure 7:
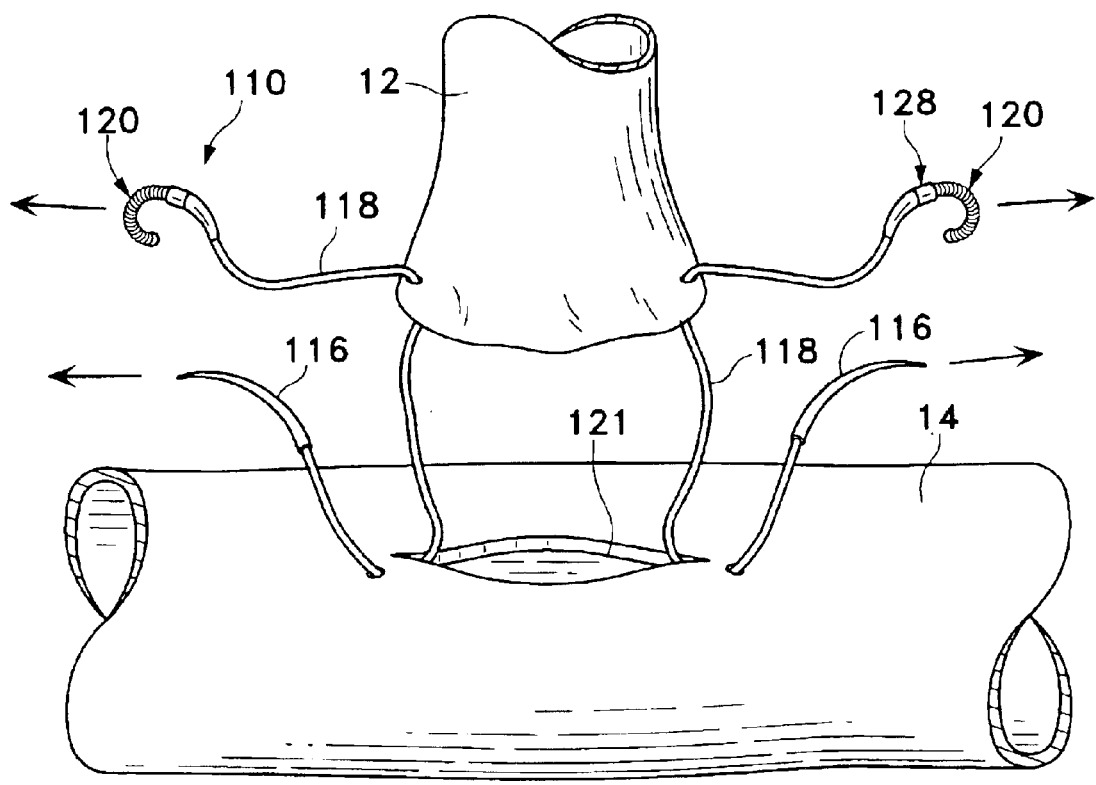
FIG. 7 shows two tissue connector assemblies of FIG. 6 in a first step for connecting a graft vessel to a target vessel.
Figure 8:
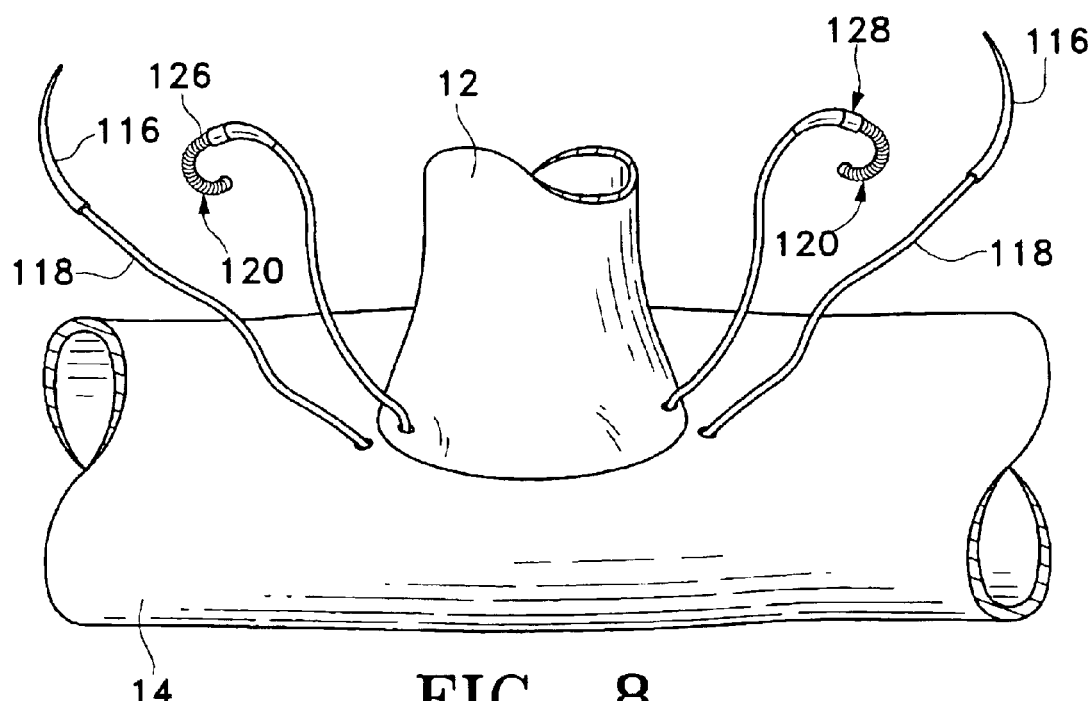
FIG. 8 shows a second step for connecting the graft vessel to the target vessel.
Figure 9:
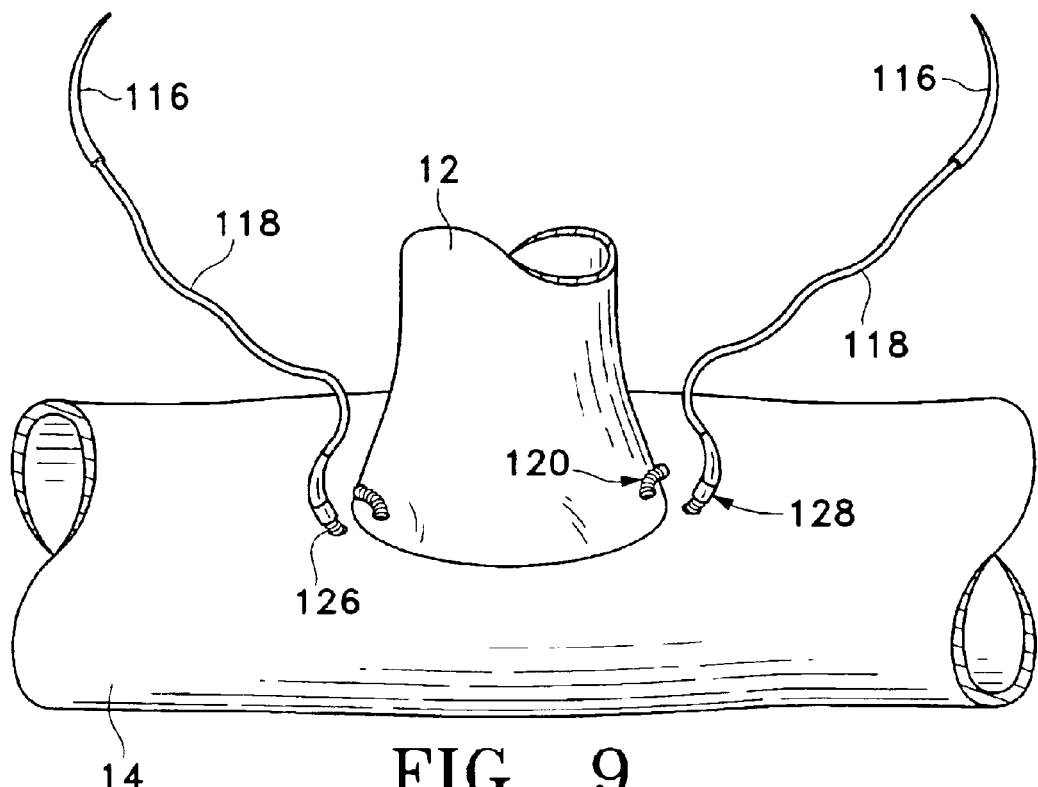
FIG. 9 shows a third step for connecting the graft vessel to the target vessel.

The patient is first prepped for standard cardiac surgery. After exposure and control of the artery 14, occlusion and reperfusion may be performed as required. Referring to FIGS. 7–9, after the arteriotomy of the snared graft vessel 12 has been made to the appropriate length, a tissue connector assembly 110 is attached to the free end of the graft vessel along an edge margin of the vessel. In order to attach the connector assembly 110, the surgeon grasps the needle 116 with a needle holder (e.g., surgical pliers, forceps, or any other suitable instrument) and inserts the needle 116 into an end margin of the graft vessel 12 in a direction from the exterior of the vessel to the interior of the vessel. The surgeon then releases the needle 116 and grasps a forward end of the needle which is now located inside the graft vessel 12 and pulls the needle and a portion of the suture 118 through the vessel. The needle 116 is passed through an opening 121 formed in the sidewall of the artery 14 and inserted into the tissue of the artery in a direction from the interior of the artery to the exterior of the artery. The surgeon then grasps the needle 116 located outside the artery 14 and pulls the needle and a portion of the suture 118 through the arterial wall. A second tissue connector assembly 110 may be inserted at a location generally 180 degrees from the location of the first tissue connector in a conventional "heel and toe" arrangement. Alternatively, a number of tissue connectors 110 may be inserted generally around the location of the heel. The graft vessel 12 may then be pulled towards the artery 14 to determine whether the opening 121 formed in the sidewall of the artery is large enough before completing the anastomosis.

Once the tissue connector assemblies 110 are inserted, the graft vessel 12 is positioned above the opening 121 in the sidewall of the artery 14 (FIG. 7). The fasteners 120 and needles 116 are pulled generally away from the artery 14 to reduce the length of the suture 118 between the vessel 12 and artery and "parachute" the vessel onto the artery (FIG. 8). The needles 116 are then pulled away from the artery 14 until the fastener 120 is positioned within the graft vessel 12 and artery with one end of each fastener extending from the vessel and the opposite end of each fastener extending from the artery (FIG. 9). The edges of the graft vessel 12 and artery 14 are positioned adjacent one another to form a continuous interior and exterior surface along the mating portions of the vessel and artery. As shown in FIG. 2C, the tissue is compressed within the fastener 120.

A surgical instrument (e.g., needle holder) is used to radially squeeze each locking device 128 to release the locking device from the fastener 120. Upon removal of the locking device 128, the coil 126 moves to its free uncompressed state which allows the wire 134 to return to its original undeformed closed position (FIG. 2A). As the wires 134 move to their closed position the adjacent tissues of the graft vessel 12 and artery 14 which were previously pulled together during the parachuting of the graft vessel onto the artery, are squeezed together to securely engage the graft vessel and artery (FIGS. 2B and 2C).

The tissue connector assemblies 1 are subsequently inserted at circumferentially spaced locations around the periphery of the graft vessel 12 to sealingly fasten the graft vessel to the artery 14. The needle 2 of the fastener 1 is inserted into the graft vessel 12 from the exterior surface of the graft vessel and pushed through the graft vessel and artery 14 tissue. The needle holder is then used to pull the needle 2 through the arterial wall. An instrument (same needle holder or other suitable instrument) is used to apply a squeezing force to the locking device 4 to release the wire 34 and coil 26 from the needle 2. This allows the coil 26 to move to its uncompressed configuration and the wire 34 to move to its closed position. It should be noted that the tissue connector assemblies 110 may remain in their open position while the tissue connector assemblies 1 are inserted into the tissue and moved to their closed position. The locking devices 128 of the tissue connector assemblies 110 may subsequently be removed from the fasteners 120 to allow the fasteners to move to their closed position. The number and combination of tissue connectors assemblies 1, 110 required to sealingly secure the connecting tissues together may vary. For example, only tissue connector assemblies 1 may be used to complete the entire anastomosis, or only tissue connector assemblies 110 may be used to connect tissues.

It should be noted that as the locking device 4 is squeezed two steps are accomplished. The fastener 10 is released from the locking device 4, thus allowing the coil 26 to uncompress and the wire 34 to move to its closed configuration, and the needle 2 is released from the fastener. Thus, in the embodiment shown, the locking device 4 provides for simultaneous actuating closure of the fastener 10 and release of the needle 2 from the fastener.

Figure 10:
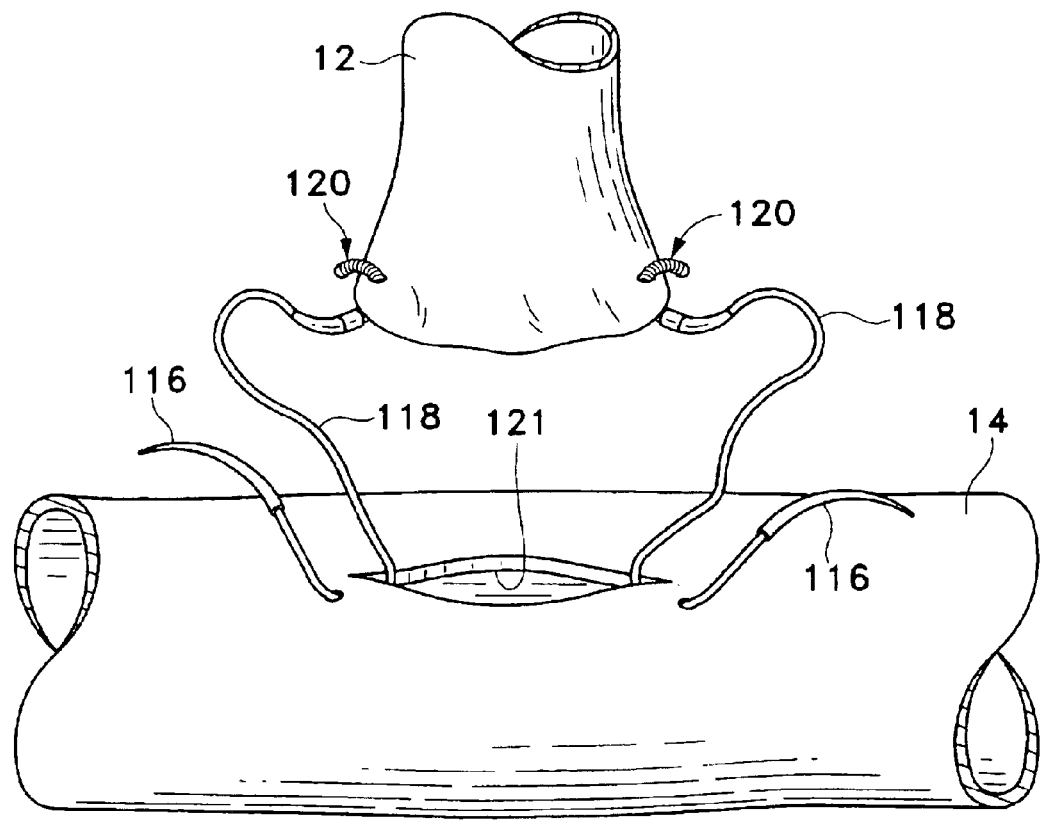
FIG. 10 shows an alternate method for connecting the graft vessel to the target vessel with the tissue connector assemblies of FIG. 6.

The graft vessel 12 may also be parachuted onto the artery 14 in the method shown in FIG. 10. The needles 116 are inserted into the graft vessel 12 and artery 14 as described above and the sutures 118 are pulled through the vessel so that the fasteners 120 are positioned within the vessel. The needles 116 are then pulled away from the artery 14 to "parachute" the graft vessel 12 onto the artery.

Although the coil 126 is shown as remaining on the wire (FIG. 6), it is to be understood that the coil 126 may also be removed from the wire 134, leaving only the wire in the connected tissue.

FIGS. 14 and 17 show exemplary uses of multiple loop tissue connector assemblies 1101 and 1502, respectively, for connecting graft vessel 12 to artery 14. In these examples, one tissue connector assembly 1101 or 1502 is threaded through two stitches. The actual number and spacing of stitches is determined by the preformed shape of multiple loop fastener 1300 or 1500, and the surgeon must select the assembly 1101 or 1502 to match the type of stitch required. As discussed previously, the wire 34 may also the shape of multiple, evenly spaced stitches or of widely or unevenly spaced stitches. The use of connector assemblies 1101 and 1502 thus permits the rapid suturing of long attachment seems in an environment with limited space, such as is encountered in endoscopic surgery. When the locking device 128c is activated, the restraining device 124c provides for the wire 34 to assume a preformed shape of the two stitches. The wire secures the tissue without the need to tie off a suture, and release causes the flexible member 118 and needle 116 to separate from the fastener for easy removal.

Figure 14A:
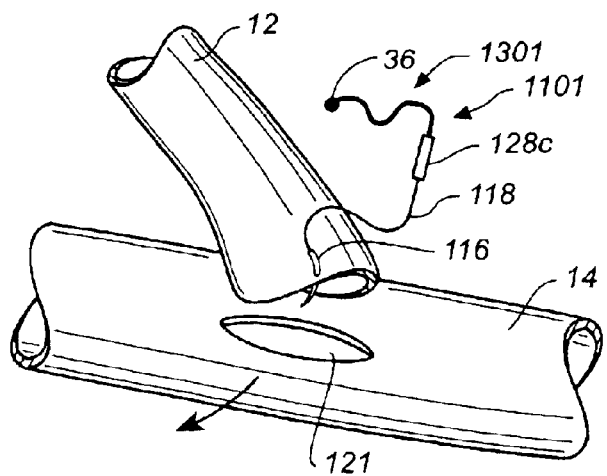
FIG. 14A–14C illustrates the use of the assembly of FIG. 11 in connecting tissue, where
Figure 14B:
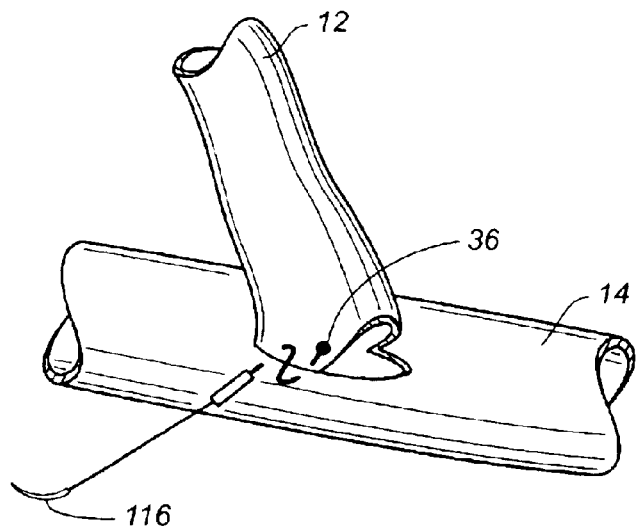
Figure 14C:
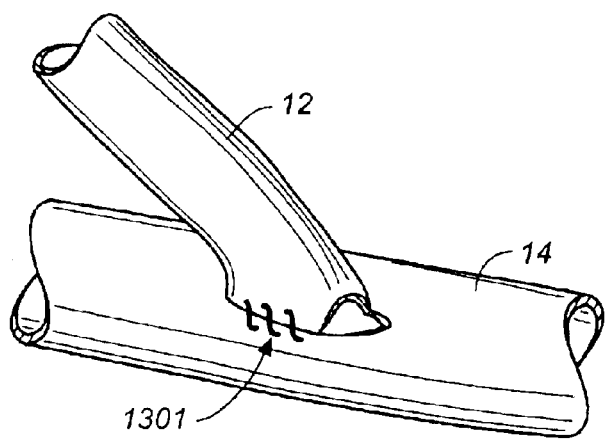

Preparation of the patient and artery 14 is similar to that described in reference to FIGS. 7–9. The surgeon selects a multiple loop fastener to execute a specific suture. In the example of FIG. 14, a double stitch is performed with a specially preformed double loop fastener 1301. The use of a single-arm multiple loop tissue connector assembly 1101, as shown in FIG. 11, in connecting tissue is illustrated in FIG. 14A–14C. Specifically, FIG. 14A shows the orientation of the tissues and the first piercing, FIG. 14B shows the threading of the fastener through the tissues, and FIG. 14C is a released fastener in the closed configuration of FIG. 13A; In order to attach the connector assembly 1301, as shown in FIG. 14, the surgeon performs two stitches with tissue connector assembly 1101. FIG. 14A shows the first stitch, in which the surgeon grasps the needle 116 with a needle holder (e.g., surgical pliers, forceps, or any other suitable instrument) and inserts the needle 116 into an end margin of the graft vessel 12 in a direction from the exterior of the vessel to the interior of the vessel. The surgeon then releases the needle 116 and grasps a forward end of the needle which is now located inside the graft vessel 12 and pulls the needle and a portion of the suture 118 through the vessel. The needle 116 is passed through an opening 121 formed in the sidewall of the artery 14 and inserted into the tissue of the artery in a direction from the interior of the artery to the exterior of the artery. The surgeon then grasps the needle 116 located outside the artery 14 and pulls the needle and a portion of the suture 118 through the arterial wall. The enlarged end 36 is large enough to prevent the pulling of the fastener 1301 through the graft vessel 12 during attachment.

A second stitch is then performed with the tissue connector assembly 1101, as shown in FIG. 14D. With both stitches threaded, the surgeon releases locking device 128c. The multiple loop fastener 1301 assumes the shape of the double stitched fastener, and the needle 116 and flexible member 118 are removed. Specifically, a surgical instrument (e.g., needle holder) is used to radially squeeze locking device 128c to release the locking device from the fastener 1301. Upon removal of the locking device 128c, the coil 26 moves to its free uncompressed state which allows the wire 34 to return to its original undeformed closed position (FIG. 13A). As the wire 34 moves to the closed position the adjacent tissues of the graft vessel 12 and artery 14 are squeezed together to securely engage the graft vessel and artery (FIGS. 14C).

As before, it is noted that as the locking device 128c is squeezed two steps are accomplished. The fastener 1301 is released from the locking device 128c, thus allowing the coil 26 to uncompress and the wire 34 to move to its closed configuration, and the flexible member 118 is released from the fastener. Thus, in the embodiment shown, the locking device 128c provides for simultaneous actuating closure of the fastener 1301 and release of the flexible member 118 and needle 116 from the fastener.

Figure 17A:
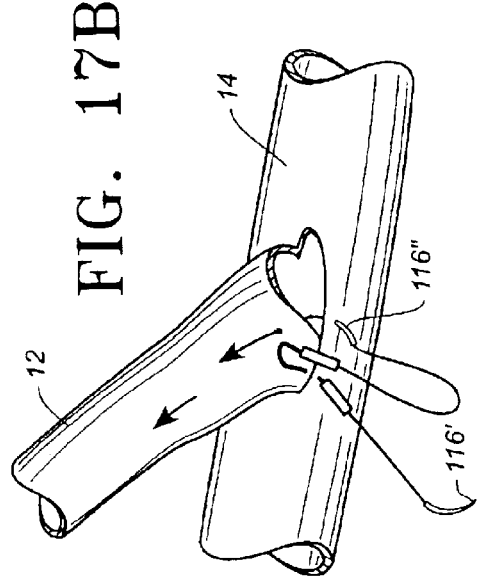
FIG. 17A–17D illustrates the use of the double-arm tissue connector assembly of FIG. 15 in connecting tissue, where
Figure 17C:
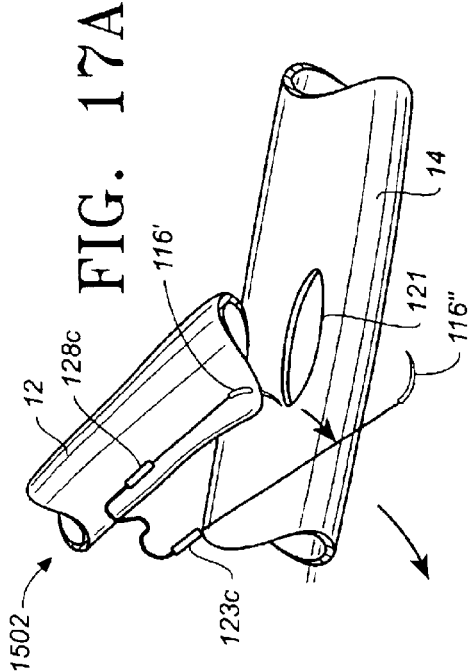

The use of the double-arm, multiple loop fastener has some similarities with that of the single arm fastener. As before, the surgeon selects a multiple loop fastener to execute a specific suture. In the example of FIG. 17, a double stitch is performed with a specially preformed double loop fastener 1501. The use of a double-arm multiple loop tissue connector assembly 1502, as in FIG. 15, is illustrated for connecting tissue in FIG. 17. FIG. 17A shows the orientation of the tissues for piercing with the first needle, FIG. 17B shows the orientation of the tissues for piercing with the second needle, FIG. 17C shows the tissue connector assembly 1502 in place before release, and FIG. 17D shows the multiple loop fastener 1501 in the closed configuration.

In order to attach the connector assembly 1502, as shown in FIG. 17, the surgeon performs one stitch with each needle 118 of tissue connector assembly 1502. FIG. 17A shows the first stitch, in which the surgeon grasps the needle 116' with a needle holder (e.g., surgical pliers, forceps, or any other suitable instrument) and inserts the needle 116' into an end margin of the graft vessel 12 in a direction from the exterior of the vessel to the interior of the vessel. The surgeon then releases the needle 116' and grasps a forward end of the needle which is now located inside the graft vessel 12 and pulls the needle and a portion of the suture 118' through the vessel. The needle 116' is passed through an opening 121 formed in the sidewall of the artery 14 and inserted into the tissue of the artery in a direction from the interior of the artery to the exterior of the artery. The surgeon then grasps the needle 116' located outside the artery 14 and pulls the needle and a portion of the suture 118' through the arterial wall.

Figure 17B:
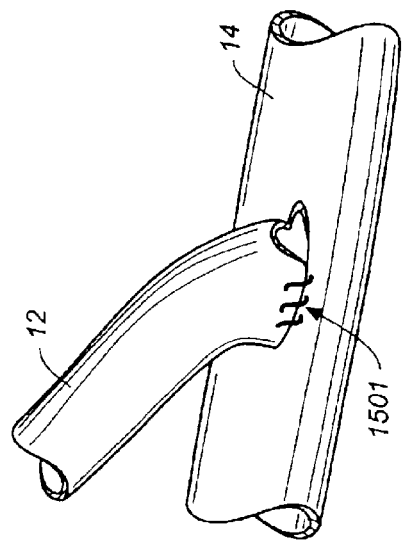
Figure 17D:
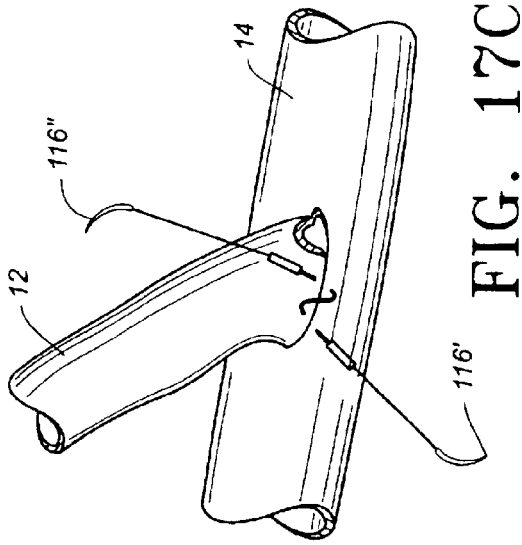

A second stitch is then performed with the tissue connector assembly 1502, as shown in FIG. 17B. The surgeon grasps the needle 116" with a needle holder (e.g., surgical pliers, forceps, or any other suitable instrument) and inserts the needle 116" through artery 14 near opening and in a direction from the exterior of the artery to the interior of the artery. The surgeon then releases the needle 116" and grasps a forward end of the needle which is now located inside the artery 14. The surgeon pulls needle 116" and a portion of the suture 118" into artery 14 and pierces an end margin of graft vessel 12. The surgeon then releases the needle 116" and grasps a forward end of the needle which is now located inside the graft vessel 14.

Both of needles 116" and 116" are pulled to located fastener 1501 as shown in FIG. 17C. The multiple loop fastener 1501 assumes the shape of the double stitched fastener, and the needles 116 and flexible members 118 are removed. Specifically, a surgical instrument (e.g., needle holder) is used to radially squeeze locking device 128c to release the locking device from the fastener 1501. Upon removal of the locking device 128c, the coil 26 moves to its free uncompressed state which allows the wire 34 to return to its original undeformed closed position (FIG. 13A). As the wire 34 moves to the closed position the adjacent tissues of the graft vessel 12 and artery 14 are squeezed together to securely engage the graft vessel and artery (FIGS. 14C).

As before, it is noted that as the locking device 128c is squeezed two steps are accomplished. The fastener 1501 is released from the locking device 128c, thus allowing the coil 26 to uncompress and the wire 34 to move to its closed configuration, and flexible members 118 are released from the fastener. Thus, in the embodiment shown, the locking device 128c provides for simultaneous actuating closure of the fastener 1501 and release of the flexible member 118 and needle 116 from the fastener.

Although the suturing procedure has been described for an end-to-side anastomosis, it should be appreciated that the procedure is applicable to an end-to-end and side-to-side anastomosis, connecting various tissue structures including single and multiple tissue structures, and puncture sites, and connecting tissue to a prosthetic graft or valve, for example.

It will be observed from the foregoing that the tissue connector assemblies of the present invention have numerous advantages. Importantly, the assemblies are easier and faster to apply than conventional sutures which require tying multiple knots. The assemblies may be used in minimally invasive procedures including endoscopic procedures, and may be inserted single handedly.

All references cited above are incorporated herein by reference.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A tissue connector assembly comprising: a fastener, where said fastener is self-closing and is movable between an open configuration and a closed configuration having a shape of two or more stitches; and at least one restraining device, where said at least one restraining device is coupled to said fastener for restraining said fastener towards said open configuration, further comprising a suture and at least one needle releasable attached to said fastener through said suture.

2. The tissue connector assembly of claim 1, wherein, when said at least one restraining device is uncoupled, said fastener moves from said open configuration towards said closed configuration.

3. The tissue connector assembly of claim 1, wherein at least a portion of said restraining device remains on said fastener when said needle is released from said fastener.

4. The tissue connector assembly of claim 1, wherein said fastener comprises a wire.

5. The tissue connector assembly of claim 4, wherein said wire has a generally circular cross-section.

6. The tissue connector assembly of claim 4 wherein said wire comprises shape memory material.

7. The tissue connector assembly of claim 1, wherein said at least one restraining device is a restraining device, wherein said fastener has a first end portion, a second end portion and an elongated member therebetween, said first end portion being coupled to said mechanical restraining device, said second end portion having a cross-sectional area greater than a cross-sectional area of said elongated member.

8. The tissue connector assembly of claim 7, further comprising a needle releasably attached to said fastener, wherein at least a portion of said restraining device remains on said fastener when said needle is released from said fastener.

9. The tissue connector assembly of claim 1, wherein said at least one restraining device includes a first restraining device and a second restraining device, wherein said fastener has a first end portion, a second end portion and an elongated member therebetween, said first end portion being coupled to said first restraining device, and said second end portion being coupled to said second restraining device.

10. The tissue connector assembly of claim 1 wherein said fastener is in a relaxed state when in said closed configuration.

11. The tissue connector assembly of claim 1 wherein said restraining device comprises a coil surrounding at least a portion of said fastener.

12. The tissue connector assembly of claim 11 wherein said coil comprises a plurality of adjacent loops, said coil being compressible with said plurality of adjacent loops being spaced closer to one another along one side of said coil than along an opposite side of said coil.

13. A tissue connector assembly comprising: a fastener, where said fastener is self-closing and is movable between an open configuration and a closed configuration having a shape of two or more stitches; and at least one restraining device, where said at least one restraining device is coupled to said fastener for restraining said fastener towards said open configuration, wherein said at least one restraining device includes a first restraining device and a second restraining device, wherein said fastener has a first end portion, a second end portion and an elongated member therebetween, said first end portion being coupled to said first restraining device, and said second end portion being coupled to said second restraining device, further comprising a first needle releasably attached to said first end portion and a second needle releasably attached to said second end portion, wherein at least a portion of each of said at least one restraining device remains on said fastener when each of said needles is released from said fastener.

14. A tissue connector assembly comprising: a fastener, where said fastener is self-closing and is movable between an open configuration and a closed configuration having a shape of two or more stitches; and at least one restraining device, where said at least one restraining device is coupled to said fastener for restraining said fastener towards said open configuration wherein said restraining device comprises a coil surrounding at least a portion of said fastener wherein each of said at least one restraining device includes a lock releasably engaging said coil, wherein engagement of said lock with said coil biases said fastener in said open configuration.

* * * * *